(12) United States Patent
Jackson et al.

(10) Patent No.: US 7,964,553 B2
(45) Date of Patent: *Jun. 21, 2011

(54) PRODUCTION PROCESSES AND SYSTEMS, COMPOSITIONS, SURFACTANTS, MONOMER UNITS, METAL COMPLEXES, PHOSPHATE ESTERS, GLYCOLS, AQUEOUS FILM FORMING FOAMS AND FOAM STABILIZERS

(75) Inventors: Andrew Jackson, West Lafayette, IN (US); Vimal Sharma, West Lafayette, IN (US); E. Bradley Edwards, Lafayette, IN (US); Janet Boggs, Crawfordsville, IN (US); Vicki Hedrick, Brookston, IN (US); Stephan Brandstadter, Indianapolis, IN (US); John Chien, West Lafayette, IN (US); Edward Norman, Chester Springs, IN (US); Robert Kaufman, St. Louis, MO (US); Bruno Ameduri, Montpellier (FR); George K. Kostov, Montpellier (FR)

(73) Assignee: E. I. Dupont de Nmeours and Company, Wilmington, DE (US)

( * ) Notice: Subject to any disclaimer, the term of this patent is extended or adjusted under 35 U.S.C. 154(b) by 530 days.

This patent is subject to a terminal disclaimer.

(21) Appl. No.: 11/899,065

(22) Filed: Sep. 4, 2007

(65) Prior Publication Data
US 2008/0108785 A1 May 8, 2008

Related U.S. Application Data

(60) Provisional application No. 60/841,936, filed on Sep. 1, 2006.

(51) Int. Cl.
C11D 1/00 (2006.01)
C11D 3/24 (2006.01)
C07C 17/00 (2006.01)
C07C 19/08 (2006.01)
C07C 21/18 (2006.01)
C07C 22/08 (2006.01)

(52) U.S. Cl. ........ 510/535; 510/475; 570/123; 570/125; 570/126; 570/138; 570/139

(58) Field of Classification Search .................. 510/475, 510/535; 570/123, 125, 126, 138, 139
See application file for complete search history.

(56) References Cited

U.S. PATENT DOCUMENTS

| | | | |
|---|---|---|---|
| 3,163,628 A | 12/1964 | Bolstad | |
| 3,287,339 A | 11/1966 | Sianesi et al. | |
| 3,331,823 A | 7/1967 | Sianesi et al. | |
| 3,335,106 A | 8/1967 | Sianesi et al. | |
| 2001/0000343 A1 | 4/2001 | Bowers | |

(Continued)

FOREIGN PATENT DOCUMENTS

WO WO 2005/074637 * 8/2005

OTHER PUBLICATIONS

Fields et al., Organophosphorus Chemistry, Journal of Chemical Society, 1970, pp. 1370-1375.

(Continued)

Primary Examiner — Brian P Mruk
(74) Attorney, Agent, or Firm — Livia Boyadjian

(57) ABSTRACT

$R_F$-compositions including surfactants, foam stabilizers, monomers, polymers, urethanes, intermediates, metal complexes, phosphate esters as well as telomerization methods are provided.

29 Claims, 8 Drawing Sheets

U.S. PATENT DOCUMENTS

Figure 1:
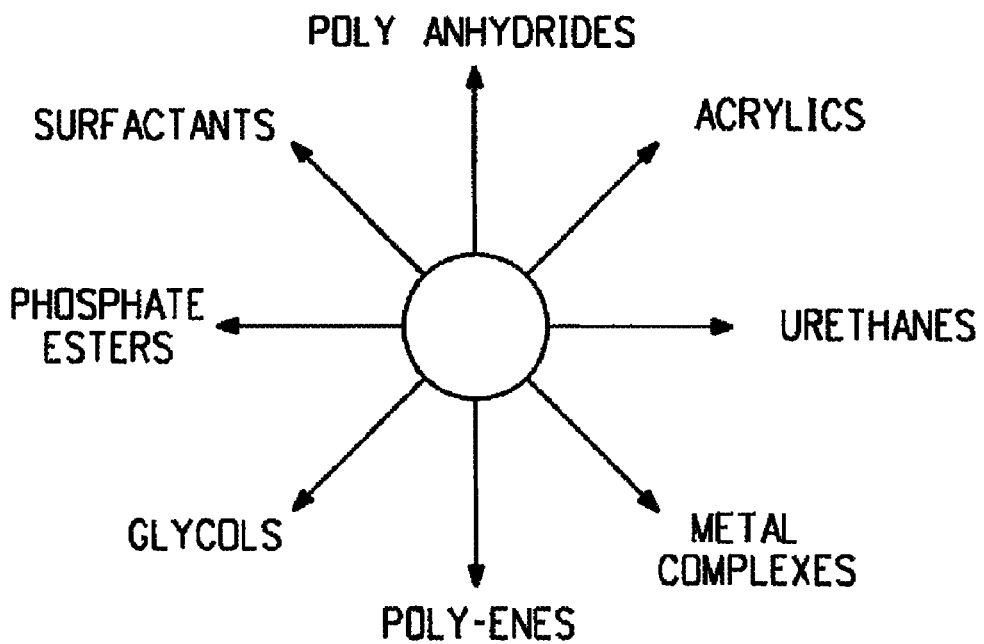

2007/0027349 A1* 2/2007 Brandstadter et al. ........ 570/172

OTHER PUBLICATIONS

Gregory et al., The Addition of Free Radicals to Unsaturated Systems, Journal of Chemical Society, 1969, pp. 991-995.

Petrov et al., Conjugate Electrophilic Iodofluorination of Fluoroolefins, J. Org. Chem., vol. 61, No. 26, 1996, pp. 9605-9607.

Petrov, Reaction of fluoroolefins with sulfur chlorides in hydrogen fluoride-boron trifluoride system, Journal of Fluorine Chemistry, 2001, pp. 325-327.

Tarrant et al., Free Radical Additions Involving Fluorine Compounds, Journal of Chemical Society, May 20, 1955, pp. 2783-2787.

Usmanov et al., VUZ, Khim i khim. tekn., 1975, pp. 464-466.

* cited by examiner

PRODUCTION PROCESSES AND SYSTEMS, COMPOSITIONS, SURFACTANTS, MONOMER UNITS, METAL COMPLEXES, PHOSPHATE ESTERS, GLYCOLS, AQUEOUS FILM FORMING FOAMS AND FOAM STABILIZERS

RELATED PATENT DATA

This patent claims priority to U.S. provisional patent application 60/841,936 which was filed Sep. 1, 2006, entitled "Production Processes and Systems, Compositions, Surfactants, Monomer Units, Metal Complexes, Phosphate Esters, Glycols, Aqueous Film Forming Foams and Foam Stabilizers" and which is incorporated by reference herein.

TECHNICAL FIELD

The present invention relates to the filed of halogenated compositions, processes for manufacturing halogenated compositions and, more specifically, fluorinated compositions, processes for manufacturing fluorinated compositions and methods for treating substrates with the fluorinated compositions.

BACKGROUND OF THE INVENTION

Compositions such as surfactants and polymers, for example, have incorporated fluorine to affect the performance of the composition when the composition is used as a treatment for materials and when the composition is used to enhance the performance of materials. For example, surfactants incorporating fluorinated functional groups can be used as fire extinguishants either alone or in formulations such as aqueous film forming foams (AFFF). Traditional fluorosurfactants, such as perfluoro-octyl sulfonate derivatives (PFOS), have linear perfluorinated portions.

Polymers incorporating fluorine have been used to treat materials. Exemplary fluorinated treatments include compositions such as Scotchguard®.

SUMMARY

Compositions and methods for making compositions such as $R_F(R_T)_nQ$ are provided. The $R_F$ group can include at least two —$CF_3$ groups, the $R_T$ group having at least two carbons, n can be at least 1 and the Q group can include one or more atoms of the periodic table of elements.

$R_F$-Intermediates and methods for making same are also provided such as $R_F(R_T)_nQ_g$, with the $Q_g$ group being one or more atoms of the periodic table of elements.

Surfactants and methods for making same are provided that can include $R_F(R_T)_nQ_S$, with the $Q_S$ group being at least one atom of the periodic table of elements and at least a portion of the $R_F$ and $R_T$ groups are hydrophobic relative to the $Q_S$ group and at least a portion of the $Q_S$ group is hydrophilic relative to the $R_F$ and $R_T$ groups.

Foam stabilizers and methods for making same are provided that can include $R_F(R_T)_nQ_{FS}$, with the $Q_{FS}$ group being at least one atom of the periodic table of elements and at least a portion of the $R_F$ and $R_T$ groups are hydrophobic relative to the $Q_{FS}$ group and at least a portion of the $Q_{FS}$ group is hydrophilic relative to the $R_F$ and $R_T$ groups.

Metal complexes and methods for making same are provided that can include $R_F(R_T)_nQ_{MC}$, with the $Q_{MC}$ group being at least one atom of the periodic table of elements.

Phosphate ester and methods of making same are provided that can include $R_F(R_T)_nQ_{PE}$, with the $Q_{PE}$ group being a portion of a phosphate ester group.

Polymers and methods of making same are provided that can include $R_F(R_T)_nQ_{MU}$, with the $Q_{MU}$ group being a portion of a polymer chain backbone.

Urethanes and methods of making same are provided that can include $R_F(R_T)_nQ_U$, with the $Q_U$ group being at least one atom of the periodic table of elements.

Glycols and methods of making same are provided that can include $R_F(R_T)_nQ_H$, with the $Q_H$ group being a portion of a glycol chain backbone.

DRAWINGS

Embodiments are described below with reference to the following accompanying drawings.

Figure 2:
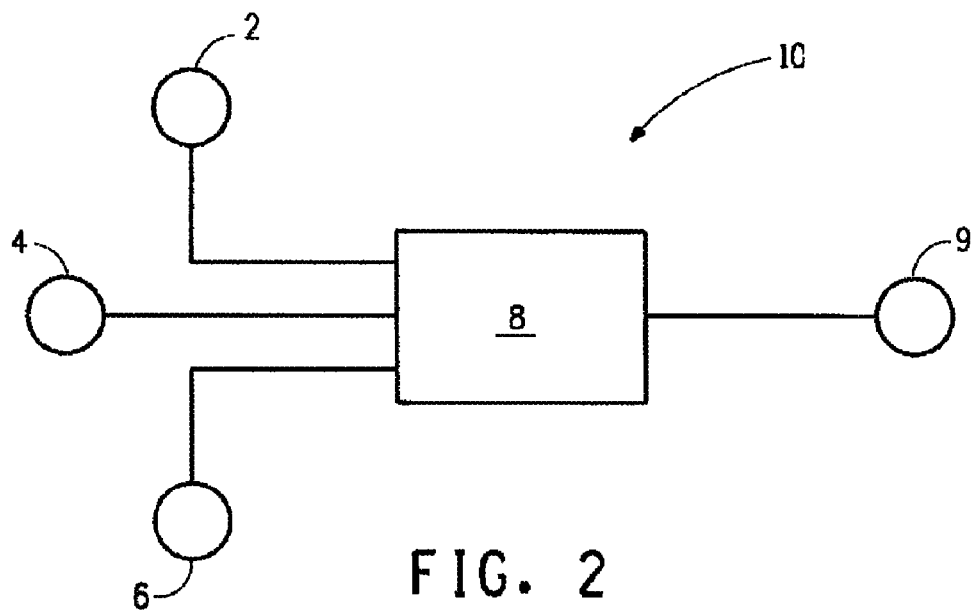
Figure 3:
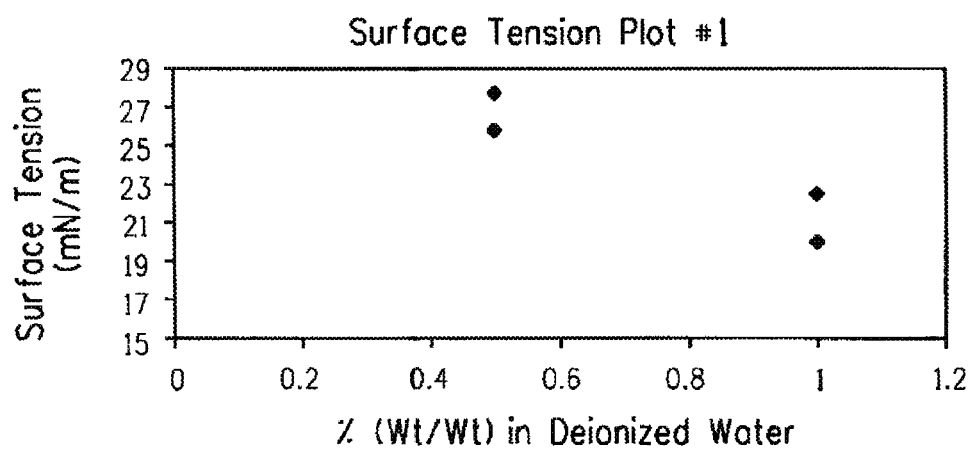
Figure 4:
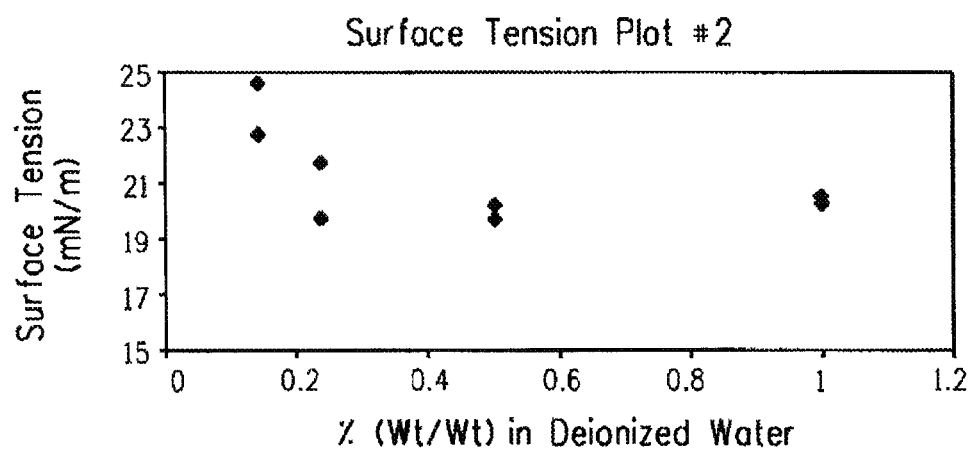
Figure 5:
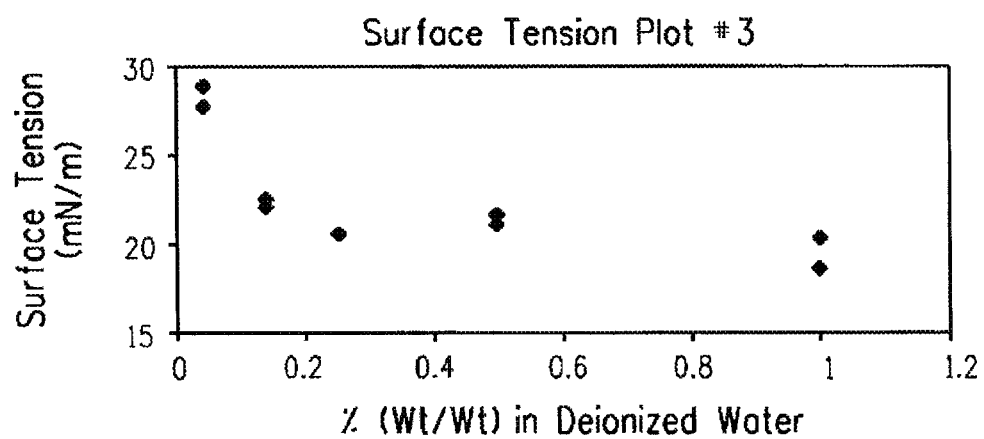
Figure 6:
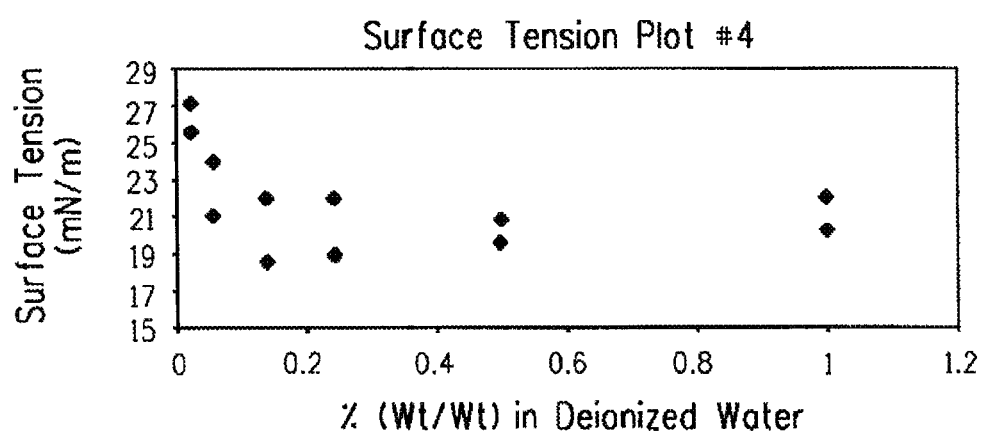
Figure 7:
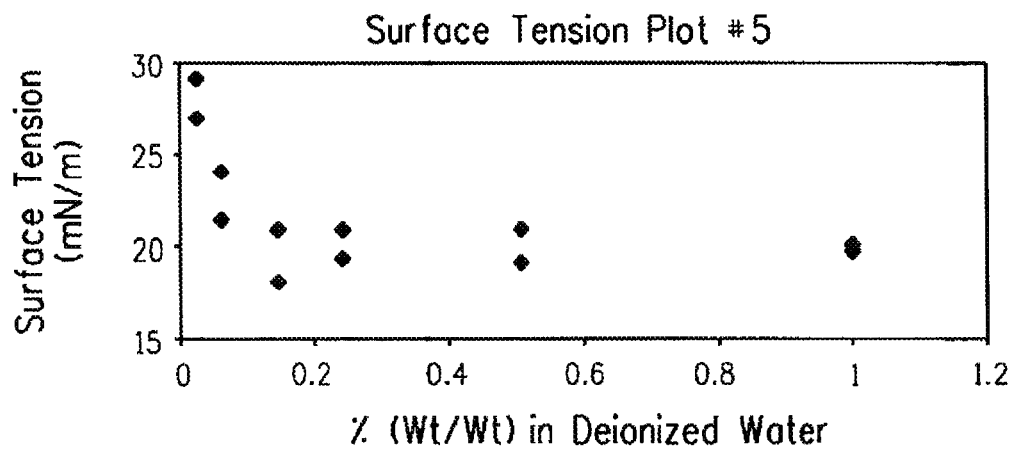
Figure 8:
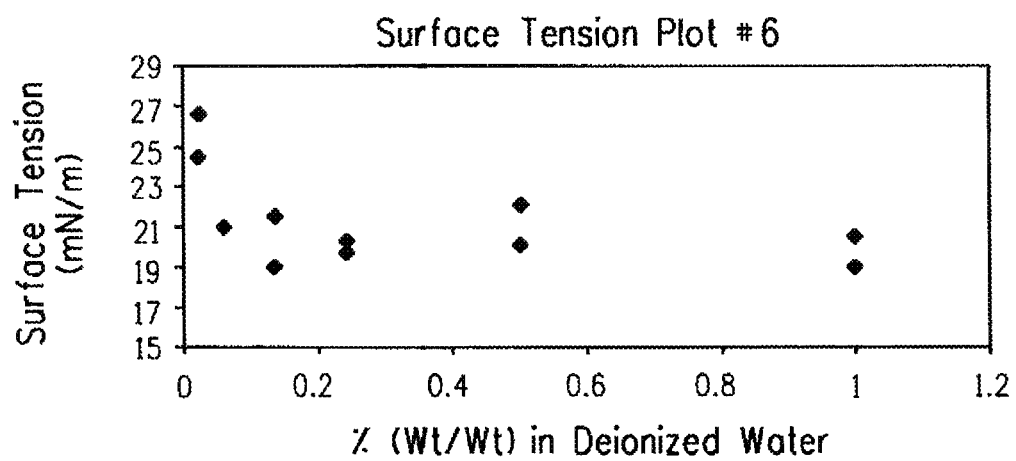
Figure 9:
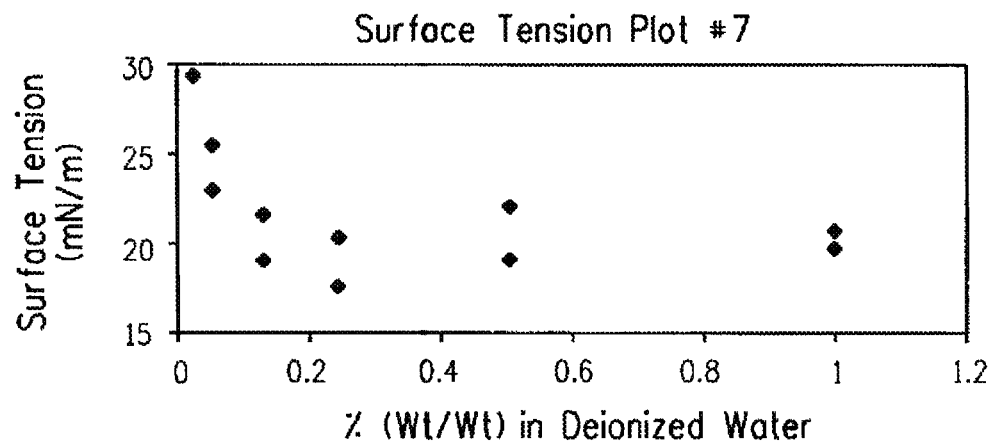
Figure 10:
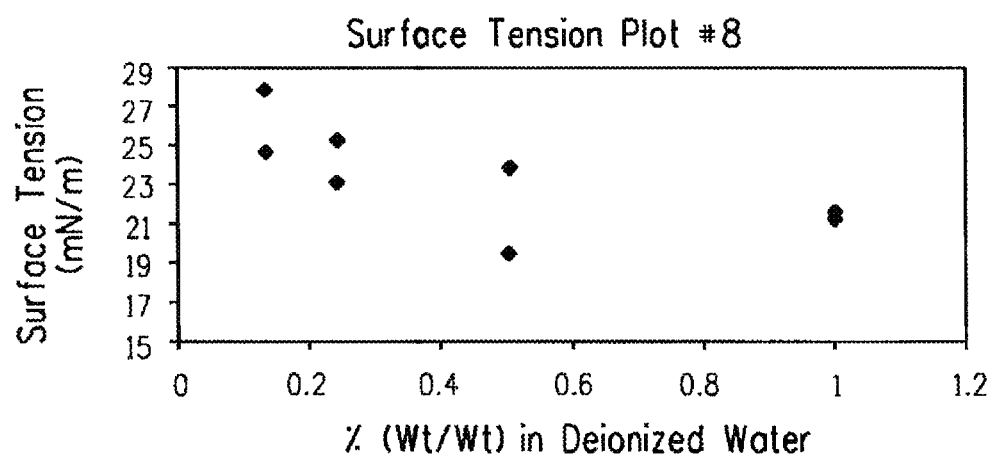
Figure 11:
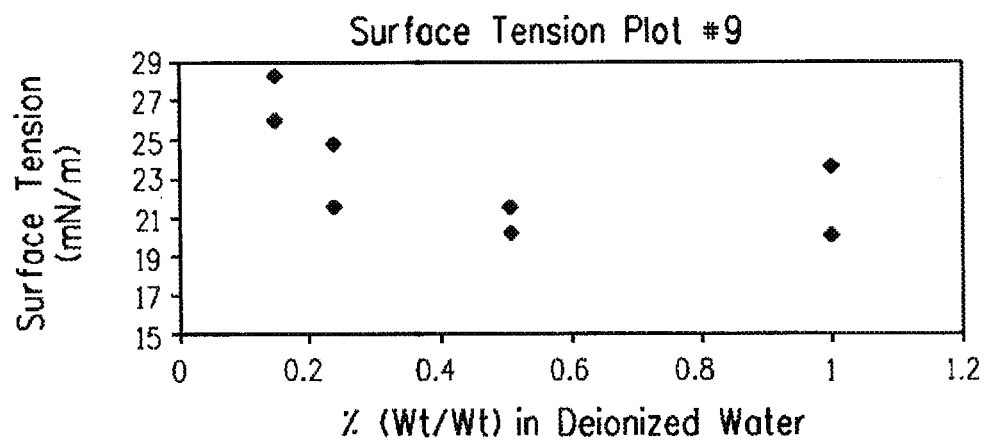
Figure 12:
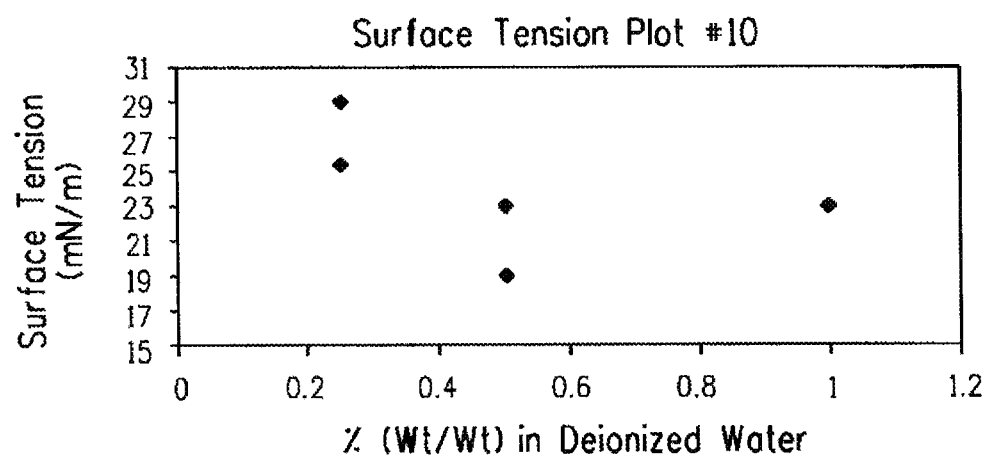
Figure 13:
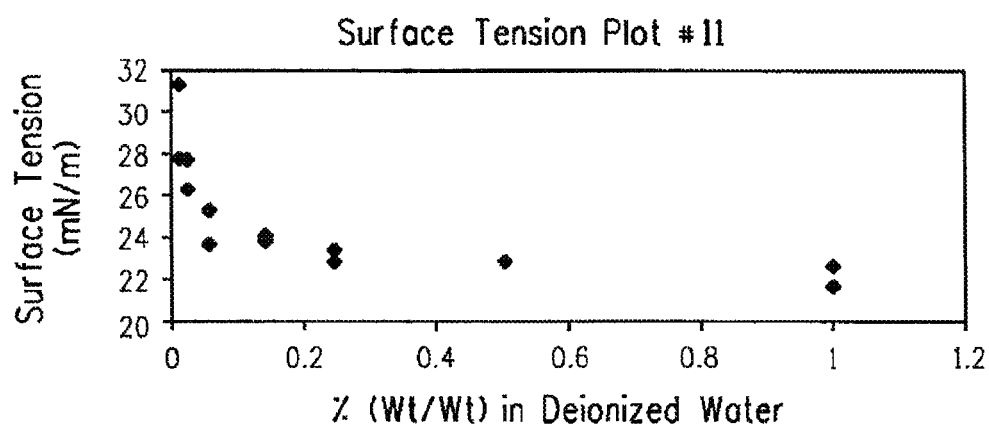
Figure 14:
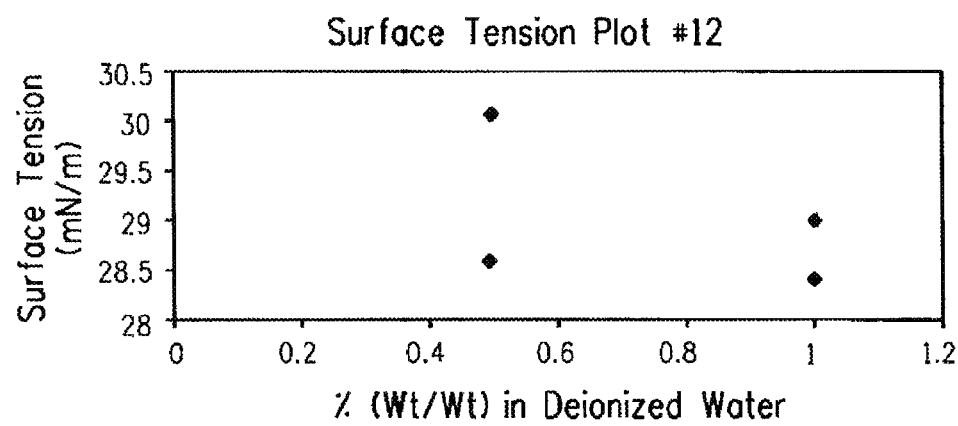
Figure 15:
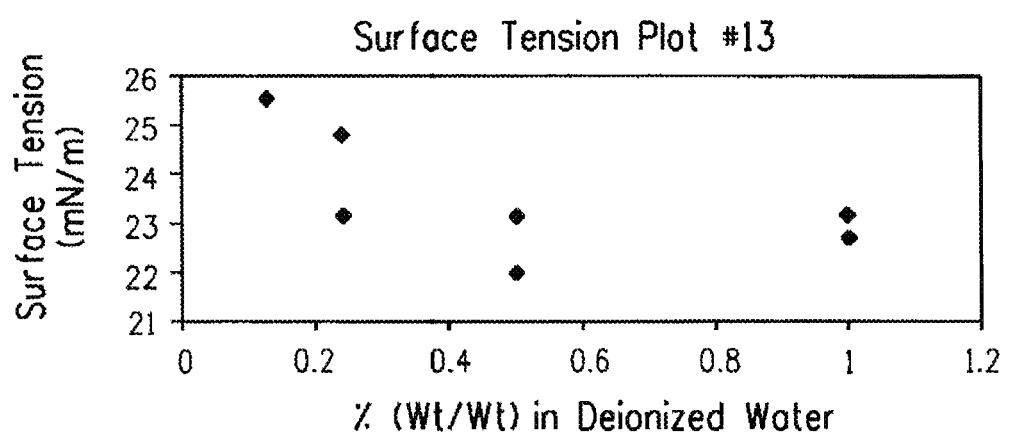

FIG. 1 is a general view of exemplary $R_F$-compositions.
FIG. 2 is an exemplary system for preparing compositions according to an embodiment.
FIG. 3 illustrates Surface Tension Plot No. 1.
FIG. 4 illustrates Surface Tension Plot No. 2.
FIG. 5 illustrates Surface Tension Plot No. 3.
FIG. 6 illustrates Surface Tension Plot No. 4.
FIG. 7 illustrates Surface Tension Plot No. 5.
FIG. 8 illustrates Surface Tension Plot No. 6.
FIG. 9 illustrates Surface Tension Plot No. 7.
FIG. 10 illustrates Surface Tension Plot No. 8.
FIG. 11 illustrates Surface Tension Plot No. 9.
FIG. 12 illustrates Surface Tension Plot No. 10.
FIG. 13 illustrates Surface Tension Plot No. 11.
FIG. 14 illustrates Surface Tension Plot No. 12.
FIG. 15 illustrates Surface Tension Plot No. 13.

DESCRIPTION

This disclosure of the invention is submitted in furtherance of the constitutional purposes of the U.S. Patent Laws "to promote the progress of science and useful arts" (Article 1, Section 8).

Exemplary $R_F$-compositions and production methods are described with reference to FIGS. 1-2. Starting materials and/or intermediate materials as well as processes for producing the same and/or introducing $R_F$-intermediates compositions into surfactants, polymers, glycols, monomers, monomer units, phosphate esters, metal complexes, and/or foam stabilizers can be described in published International Patent applications: PCT/US05/03429, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; PCT/US05/02617, entitled Compositions, Halogenated Compositions, Chemical Production and Telomerization Processes, filed Jan. 28, 2005; PCT/US05/03433, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; PCT/US05/03137, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; and PCT/US05/03138, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005, the entirety of all of which are incorporated by reference herein ("Published International Applications").

Referring to FIG. 1, a general view of exemplary $R_F$-compositions is shown. $R_F$-compositions include, but are not limited to, $R_F$-surfactants, $R_F$-monomers, $R_F$-monomer units, $R_F$-metal complexes, $R_F$-phosphate esters, $R_F$-glycols, $R_F$-urethanes, and or $R_F$-foam stabilizers. In exemplary embodiments, poly-anhydrides, acrylics, urethanes, metal complexes, poly-enes, and/or phosphate esters can include $R_F$ portions as well.

$R_F$-compositions include compositions that have an $R_F$ portion and/or $R_F$ portions. The $R_F$ portion can be $R_F$ groups, such as pendant groups and/or moieties of compositions. The $R_F$ portion can include at least two —$CF_3$ groups and the —$CF_3$ groups may be terminal. The $R_F$ groups can be —$C_3F_6$ or —$C_3F_7$, for example. The $R_F$ portion can also include both —$CF_3$ groups and additional groups containing fluorine, such as —$CF_2$— groups. In exemplary embodiments, the $R_F$ portion can include a ratio of —$CF_2$— groups to —$CF_3$— groups that is less than or equal to two, such as $(CF_3)_2CF$— groups. The $R_F$ portion can also include three pendant —$CF_3$ groups, in other embodiments. The $R_F$ portion can include at least three pendant —$CF_3$ groups and at least one —$CF_2$— group. The $R_F$ portion can include at least three pendant —$CF_3$— groups, at least one —$CF_2$— group and at least five —$CH_2$—, in exemplary embodiments. In exemplary embodiments, the $R_F$ portion can include a ratio of —$CF_2$— groups to —$CH_2$— groups that can be 0.4 to 1. The $R_F$ portion can include, in exemplary embodiments a ratio of —$CF_2$— groups to —$CF_3$— groups that can be 0.4 to 1. The $R_F$ portion can be a 1,1,1,2,4,4,6,6,13,13,13-undecafluoro-2,8,10-tris(trifluoromethyl)tridecyl group, for example.

The $R_F$-compositions can include $R_F(R_T)_nQ$, where the $R_F$ group has a carbon amount greater than C5 and at least one terminal and at least one pendant —$CX_3$ group, with X being one or both of H and F, for example. The $R_F$ group can have carbon amount between C5 and C17. Example $R_F$ groups can include $(CF_3)_2C_F(CH_2CF_2)_l$—, with l being from 1 to 2; $(CF_3)_2CF(CH_2C(CF_3)H)_m$—, with m being from 1 to 3; and/or $(CF_3)_2CF(CH_2CF_2)_l(CH_2C(CF_3)H)_m$—, with l being from 1 to 2 and m being from 1 to 3.

More particularly, the $R_F$ groups can be one or more of: $(CF_3)_2CFCH_2CH(CF_3)$—, $(CF_3)_2CFCH_2C(CF_3)HCH_2$—, $(CF_3)_2CFCH_2C(CF_3)HCH_2CF_2$—, $(CF_3)_3CCH_2C(CF_3)H$—, $(CF_3)_2CFCH_2CF_2$—, $(CF_3)_2CFCH_2CF_2CH_2$—, $(CF_3)_2CFCH_2CF_2CH_2CF_2$—, $(CF_3)_2CFCH_2CF_2CH_2CF_2CH_2$—, $(CF_3)_2CFCH_2CF_2CH_2CF_2CH_2C(CF_3)H$—, $(CF_3)_2CFCH_2CF_2CH_2CF_2CH_2C(CF_3)HCH_2C(CF_3)H$—, $(CF_3)_2CFCH_2CF_2CH_2CF_2CH_2C(CF_3)HCH_2C(CF_3)H$—, and/or $(CF_3)_2CFCH_2CF_2CFH_2CF_2CH_2C(CF_3)HCH_2C(CF_3)HCH_2C(CF_3)H$—. According to exemplary embodiments, the $R_F$ group can further comprise at least a portion of an $(R_T)$ group or groups.

The $R_T$ group can include at least one C-2 group. The $R_T$ group can include a C-3 group and be incorporated into and form a part of $R_F$ groups via processes described herein, such as addition reactions employing a carbon nucleophile. The $R_T$ group can be —$C_nH_{2n}$— wherein n is at least 1, for example. The $R_T$ group can be butyl, in exemplary embodiments. The $R_T$ group can be —$CH_2CX_2$—, with X being H and/or F, for example. The $R_T$ group can be —$CH_2CH_2$— and/or —$CH_2CF_2$—. The $R_T$ group can be one or more of: —$CH_2CF_2CH_2CH(CF_3)$—, —$CF_2CH_2CF_2CH_2CH(CF_3)$—, —$CH_2CF_2CH_2CF_2CH_2CH(CF_3)$—, —$CF_2CH_2CH(CF_3)CH_2$—, —$CF_2CH_2CH(CF_3)CH_2CH(CF_3)$—, —$CF_2CH_2CH(CF_3)CH_2CH(CF_3)CH_2$—, and/or —$CF_2CH_2CH(CF_3)CH_2CH(CF_3)CH_2CH(CF_3)$—. The $R_T$ group can repeat in units and the units can be designated as n with n being greater than 1. In example implementations these $R_T$ groups can be incorporated into and form a part of $R_F$ groups via processes described herein, such as telomerization processes.

In exemplary implementations, $R_F$-compositions can demonstrate desirable surface energies, affect the surface tension of solutions to which they are exposed, and/or affect the environmental resistance of materials to which they are applied and/or incorporated. Exemplary compositions include, but are not limited to, substrates having $R_F$-compositions thereover and/or liquids having $R_F$-compositions therein. $R_F$ portions can be incorporated into compositions such as polymers, acrylate monomers and polymers, glycols, fluorosurfactants, and/or AFFF formulations. These compositions can be used as dispersing agents or to treat substrates such as textile fabric, textile yarns, leather, paper, plastic, sheeting, wood, ceramic clays, as well as, articles of apparel, wallpaper, paper bags, cardboard boxes, porous earthenware, construction materials such as brick, stone, wood, concrete, ceramics, tile, glass, stucco, gypsum, drywall, particle board, chipboard, carpet, drapery, upholstery, automotive, awning fabrics, and rainwear. $R_F$-compositions can be prepared from $R_F$-intermediates.

$R_F$ portions can be incorporated into $R_F$-compositions and/or can be starting materials for $R_F$-compositions via $R_F$-intermediates. Exemplary $R_F$-intermediates include an $R_F$ portion described above, as well as at least one functional portion that allows for incorporation of the $R_F$ portion into compositions to form $R_F$-compositions. The Q group of the $R_F$-composition can be a $Q_g$ group for $R_F$-intermediates and this $Q_g$ group can be the functional portion. Functional portions can include halogens (e.g., iodine), mercaptan, thiocyanate, sulfonyl chloride, acid, acid halides, hydroxyl, cyano, acetate, allyl, epoxide, acrylic ester, ether, sulfate, thiol, phosphate, and/or amines, for example. Without incorporation and/or reaction, $R_F$-intermediates can include $R_F$-compositions, such as $R_F$-monomers and/or ligands of $R_F$-metal complexes, for example.

$R_F$-intermediates can include $R_F$-$Q_g$ with $R_F$ representing the $R_F$ portion and $Q_g$ representing, for example, the functional portion, and/or, as another example, an element of the periodic table of elements. In exemplary embodiments, $Q_g$ is not a proton, methyl, and/or a methylene group. Exemplary $R_F$-intermediates include, but are not limited to, those in Table 1 below.

TABLE 1

Exemplary $R_F$-Intermediates

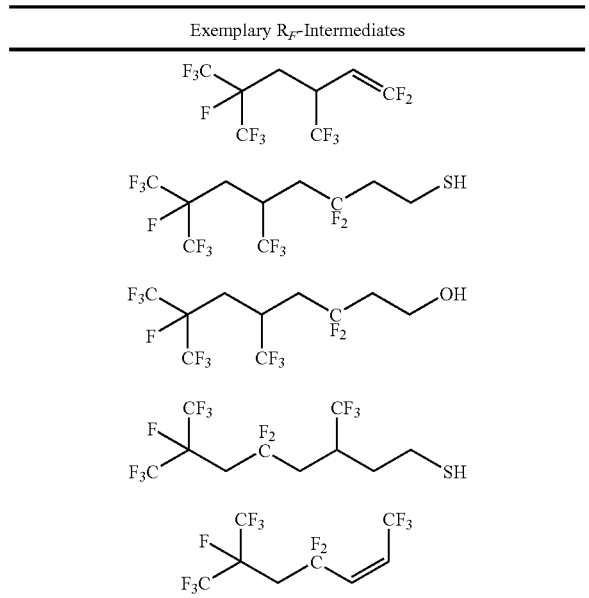

TABLE 1-continued

Exemplary R$_F$-Intermediates

[Structures of exemplary R$_F$-Intermediates]

Utilizing the systems and methods to prepare starting materials and/or reaction products described in the Published International Applications, novel R$_F$-Intermediates can be prepared according to examples 1-15 below.

(1)

1,1,1,2,4,4,7,7,7-nonafluoro-2-(trifluoromethyl)-6-iodoheptane
→ Base →
1,1,1,4,4,6,7,7,7-nonafluoro-6-(trifluoromethyl)hept-2-ene (2)

1,1,1,2,4,4-hexafluoro-2,6-bis(trifluoromethyl)-8-iodooctane
→ 1. Thiourea 2. NaOH →
5,5,7,8,8,8-hexafluoro-3,7-bis(trifluoromethyl)octane-1-thiol (3)

1,1,1,2,4,4-hexafluoro-2,6-bis(trifluoromethyl)-8-iodooctane
→ 20% Fuming H$_2$SO$_4$ / Na$_2$SO$_3$ (aq) →
5,5,7,8,8,8-hexafluoro-3,7-bis(trifluoromethyl)octan-1-ol (4)

1,1,1,2,4,4-hexafluoro-2,6-bis(trifluoromethyl)-8-iodooctane
→ Base →
5,5,7,8,8,8-hexafluoro-3,7-bis(trifluoromethyl)oct-1-ene (5)

1,1,1,2,6,6-hexafluoro-2,4-bis(trifluoromethyl)-6-iodohexane
→
1,1,5,6,6,6-hexafluoro-3,5-bis(trifluoromethyl)hex-1-ene (6)

1,1,1,2,6,6-hexafluoro-2,4-bis(trifluoromethyl)-8-iodooctane
→ 20% Fuming H2SO4 / Na2SO3 (aq) →

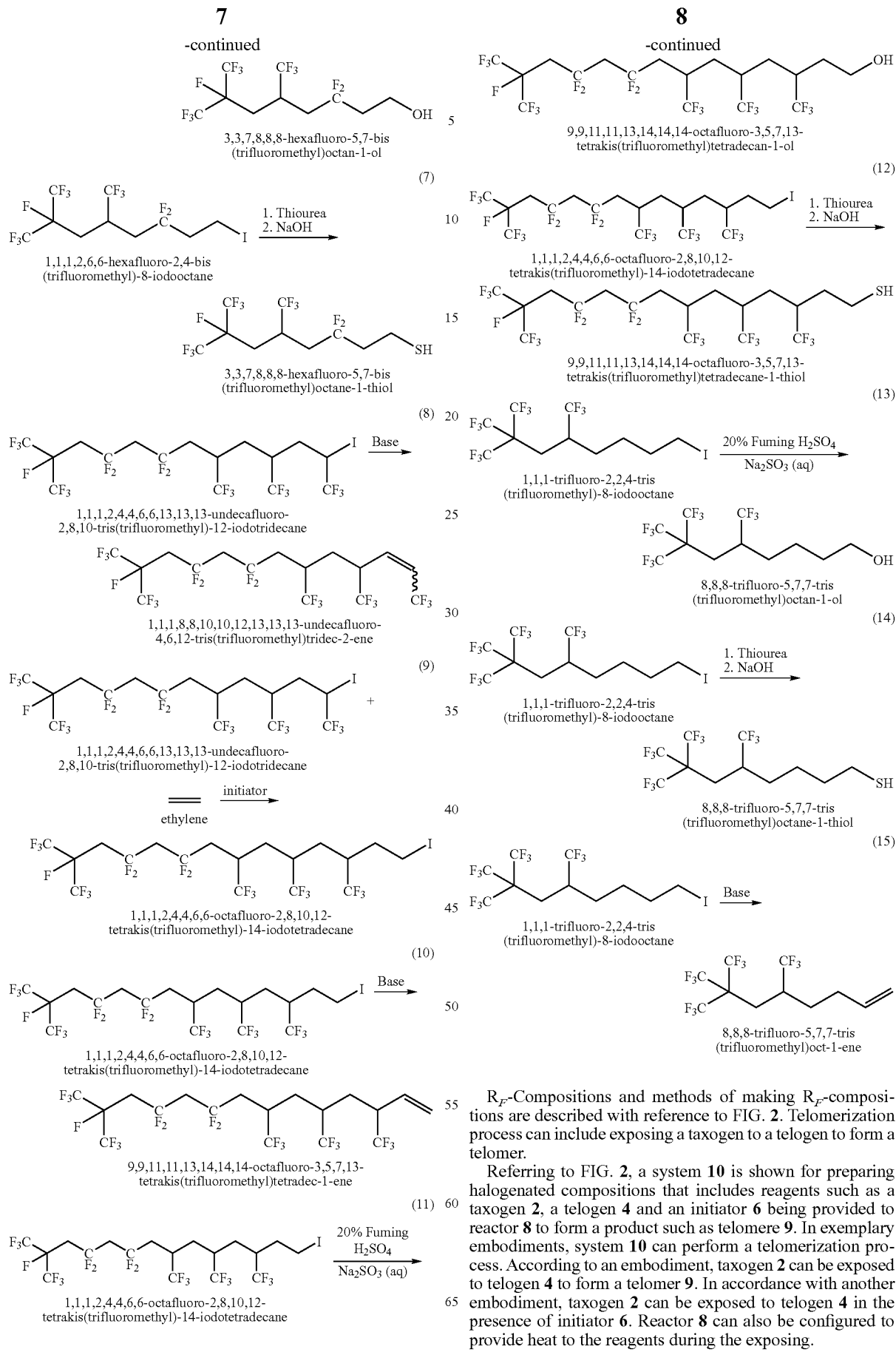

$R_F$-Compositions and methods of making $R_F$-compositions are described with reference to FIG. 2. Telomerization process can include exposing a taxogen to a telogen to form a telomer.

Referring to FIG. 2, a system 10 is shown for preparing halogenated compositions that includes reagents such as a taxogen 2, a telogen 4 and an initiator 6 being provided to reactor 8 to form a product such as telomere 9. In exemplary embodiments, system 10 can perform a telomerization process. According to an embodiment, taxogen 2 can be exposed to telogen 4 to form a telomer 9. In accordance with another embodiment, taxogen 2 can be exposed to telogen 4 in the presence of initiator 6. Reactor 8 can also be configured to provide heat to the reagents during the exposing.

Taxogen 2 can include at least one $CF_3$-comprising compound. The $CF_3$-comprising compound can have at least two carbons. In exemplary embodiments, taxogen 2 can comprise an olefin, such as 3,3,3-trifluoropropene (TFP, trifluoropropene), ethylene (ethene), 1,1-difluoroethene (VDF), 1,1,3,3,3-pentafluoropropene (PFP, pentafluropropene). In exemplary embodiments, taxogen 42 can include TFP and telogen 44 can include $(CF_3)_2CFI$ with a mole ratio of taxogen 42 to telogen 44 being from about 0.2:1 to about 10:1, from about 1:1 to about 5:1, and/or from about 2:1 to about 4:1. Taxogen 2 can include 4,5,5,5-tetrafluoro-4-(trifluoromethyl)pent-1-ene and/or 6,7,7,7-tetrafluoro-6-(trifluoromethyl)hept-1-ene and telogen 4 can include $(CF_3)_2CFI$, for example.

According to additional embodiments, taxogen 2 can include those compounds shown below in Table 2.

TABLE 2

Exemplary Taxogens

=$CF_2$ (structures)

Telogen 4 can include halogens such as fluorine and/or chlorine. Telogen 4 can include at least 4 fluorine atoms and can be represented as $R_FQ$ and/or $R_{Cl}Q$. The $R_F$ group can include at least four fluorine atoms and the Q group can include one or more atoms of the periodic table of elements. Exemplary $R_F$ groups can include: $(CF_3)_2CFCH_2CH(CF_3)$ $CHCF_2$—; $(CF_3)_2CFCH_2CF_2CH_2CH(CF_3)$—; $(CF_3)_2$ $CFCH_2CF_2CH_2CF_2CH_2CH(CF_3)CH_2CH(CF_3)CH_2CH$ $(CF_3)$—.

$R_F$-Q can be 1,1,1,2,3,3,3-heptafluoro-2-iodopropane (2-iodoheptafluoropropane, i-$C_3F_7I$, $F_7I$), for example. Exemplary telogens can include the halogenated compounds described above, such as $(CF_3)_2CF$—, $C_6F_{13}I$, trichloromethane, $HP(O)(OEt)_2$, $BrCFClCF_2Br$, R—SH(R being a group having at least one carbon) and/or ROH(R being a group having at least one carbon). The Q group can be H or I with the $R_F$ group being $(CF_3)_2CF$— and/or —$C_6F_{13}$, for example. The RCl group can include at least one —$CCl_3$ group.

According to additional embodiments, telogen 4 can include those compounds shown below in Table 3. As exemplary implementations are shown in Table 3 below, telogens can be products of telomerizations.

TABLE 3

Exemplary Telogens

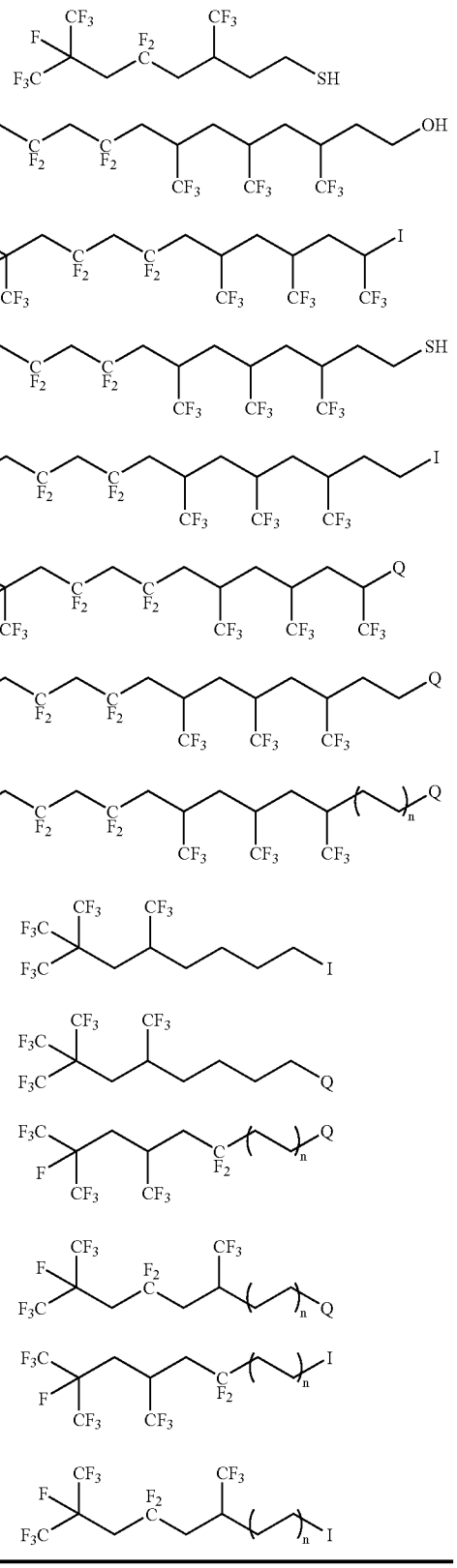

In exemplary embodiments, taxogen 2 can include trifluoropropene and telogen 4 can include $(CF_3)_2CFI$, with a mole ratio of taxogen 2 to telogen 4 being from about 1:1 to about 1:10, 1:4 to about 4:1, and/or to about 2:1 to about 4:1.

Reactor 8 can be any lab-scale or industrial-scale reactor and, in certain embodiments, reactor 8 can be configured to control the temperature of the reagents therein. According to exemplary embodiments reactor 8 can be used to provide a temperature during the exposing of the reagents: of from about 90° C. to about 180° C.; of from about 60° C. to about 220° C.; and/or of from about 130° C. to about 150° C.

According to example implementations, the taxogen can be one or more of VDF, TFP, and ethylene, and the telogen can include one of $C_3F_6(R_T)_nX$ or $C_3F_7(R_T)_nX$, wherein X is a halogen. The $R_T$ can be one or both of $—CH_2CF_2—$ and $—CH_2C(CF_3)H—$, and n is 1 to 4. More particularly: the taxogen can be VDF and the telogen can be $(CF_3)_2CFCH_2CH(CF_3)I$; the taxogen can be TFP and the telogen can be $(CF_3)_2CFCH_2CF_2I$; the taxogen can be TFP and the telogen can be $(CF_3)_2CFCH_2CF_2CH_2CF_2I$; the taxogen can be TFP and the telogen can be $(CF_3)_2CFCH_2CF_2CH_2CF_2CH_2CH(CF_3)I$; the taxogen can be TFP and the telogen can be $(CF_3)_2CFCH_2CF_2CH_2CF_2CH_2CH(CF_3)CH_2CH(CF_3)I$; the taxogen can be ethylene and the telogen can be $(CF_3)_2CFCH_2CF_2CH_2CF_2CH_2CH(CF_3)CH_2CH(CF_3)CH_2CH(CF_3)I$; and the taxogen can be ethylene and the telogen can be $(CF_3)_3CCH_2CH(CF_3)I$.

Telomerization processes can also include exposing a taxogen to a telogen to form a telomer, with the taxogen comprising an olefin having greater than two carbon atoms, and the telogen comprising at least five carbon atoms and having at least two $—CF_3$ groups. As an example, the taxogen can be one of ethylene, VDF, TFP, VDF, 4,5,5,5-tetrafluoro-4-(trifluoromethyl)pent-1-ene and/or 6,7,7,7-tetrafluoro-6-(trifluoromethyl)hept-1-ene.

Telomer 9, produced upon exposing taxogen 2 to telogen 4, can include $R_F(R_T)_nQ$ and/or $R_{Cl}(R_T)_nH$. The $R_T$ group can include at least one C-2 group having a pendant $—CF3$ group, such as

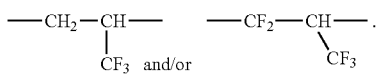

Exemplary products include

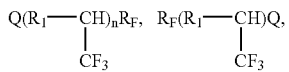

and/or one or both of

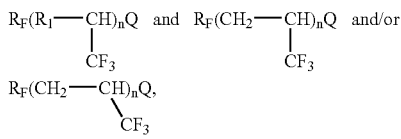

with $R_1$ including at least one carbon atom, such as $—CH_2—$ and/or $—CF_2—$, for example. $R_T$ can also include $—CH_2—CF_2—$; $—CH_2—(CH_2CF(CF_3)_2)CH—$; and/or $—CH_2—CH_2—$. In exemplary embodiments, n can be at least 1 and in other embodiments n can be at least 2 and the product can include one or more of

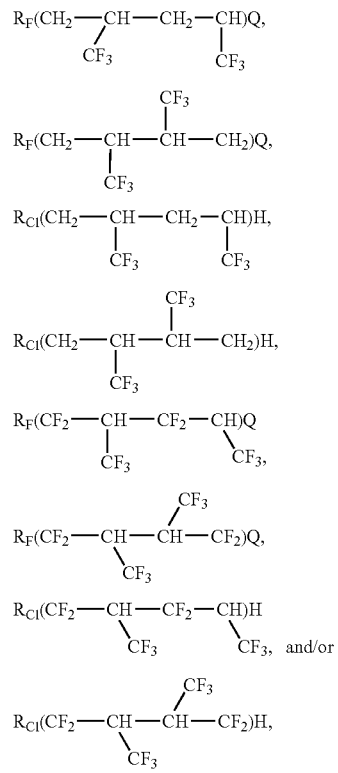

for example. According to other implementations n can be 3 or even at least 4. In exemplary embodiments, n can be at least 1 and in other embodiments n can be at least 2 and the product can include one or more of

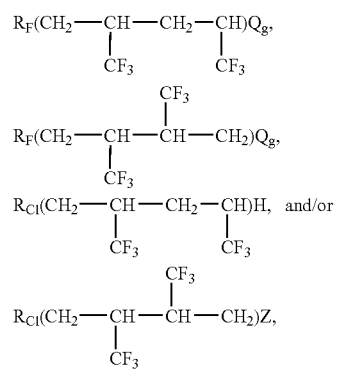

being H, Br, and/or Cl, for example

In an exemplary embodiment, the taxogen trifluoropropene can be exposed to the telogen $(CF_3)_2CFI$ to form the telomer

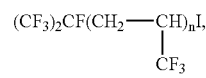

and, by the way of another example, trifluoropropene can be exposed to the telogen C$_6$F$_{13}$I to form the telomer

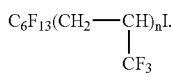

In an exemplary embodiment, the taxogen trifluoropropene can be exposed to the telogen (CF$_3$)$_2$CFI to form the telomer

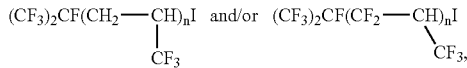

and, by the way of another example, trifluoropropene can be exposed to the telogen C6F13I to form the telomer

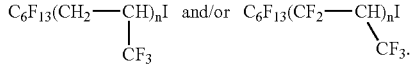

In accordance with another embodiment, the taxogen trifluoropropene can also be exposed to the telogen CCl$_3$Z, (Z=H, Br, and/or Cl, for example) to form the telomer

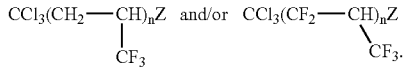

Products having n being at least 2 can be formed when utilizing an excess of the taxogen as compared to the telogen. For example, at least a 2:1 mole ratio of the taxogen to the telogen can be utilized to obtain products having n being at least 2. For example and by the way of example only, at least two moles of the taxogen trifluoropropene can be exposed to at least one mole of the telogen (CF$_3$)2CFI to form one or both of the telomers

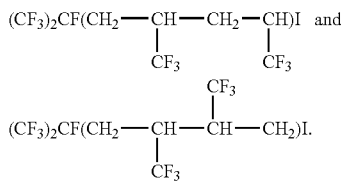

According to exemplary embodiments, telomer 9 can include those compounds shown in Table 4 below. As exemplary implementations are shown in Table 4 below, telomers can also be utilized as telogens.

Heterotelomerization can also be accomplished via cotelomerization and/or oligotelomerization. As an example, at least two different taxogens may be combined with at least one telogen to facilitate the production of at least a cotelomer. As another example, telomers may be produced from a first taxogen and the product telomer my be used in a subsequent telomerization with a second taxogens different from the first taxogen.

TABLE 4

Exemplary Telomers

[Structures shown]

In additional embodiments initiator 6 may be provided to reactor 8 during the exposing of the reagents. Initiator 6 can include thermal, photochemical (UV), radical, and/or metal complexes, for example, including a peroxide such as di-tert-butyl peroxide. Initiator 6 can also include catalysts, such as Cu. Initiator 6 and telogen 4 can be provided to reactor 8 at a mole ratio of initiator 6 to taxogen 2 of from between about 0.001 to about 0.05 and/or from between about 0.01 to about 0.03, for example.

According to exemplary embodiments, various initiators 6 and telogens 4 can be used to telomerize taxogen 2 as referenced in Table 5 below. Telomerizations utilizing photochemical and/or metal-complex initiators 6 can be carried out in batch conditions using Carius tube reactors 8. Telomerizations utilizing thermal and/or peroxide initiators 6 can be carried out in 160 and/or 500 cm$^3$ Hastelloy reactors 8.

An embodiment of the disclosure provides R$_F$-surfactant compositions that include the R$_F$ portions described above. Exemplary R$_F$-surfactant compositions can be referred to as R$_F$-Q$_S$. According to exemplary embodiments the R$_F$ portion can at least partially include an R$_F$(R$_T$)n portion as described above. The R$_F$(R$_T$)n portion of the surfactant can also include the R$_S$ portion described above. In accordance with exemplary implementations the R$_S$ portion can be incorporated to provide additional carbon between the R$_F$ and/or R$_F$(R$_T$)n portions and the Q$_s$ portion of the surfactant. Exemplary R$_s$ portions include —CH$_2$—CH$_2$—. As an example, the surfactant composition can comprise R$_F$(R$_T$)$_n$Q$_s$. The R$_F$ group can comprise at least one —CF$_3$ group. The R$_T$ group can comprise —CF$_2$CH$_2$CH(CF$_3$)—, with n being at least one. The Q$_S$ group can be at least one atom of the periodic table of elements, wherein at least a portion of the R$_F$ and R$_T$ groups are hydrophobic relative to the Q$_S$ group, and at least a portion of the Q$_s$ group is hydrophilic relative to the R$_F$ and R$_T$ groups.

In a system having at least two parts, R$_F$ can have a greater affinity for a first part of the system than Q$_s$, and Q$_s$ can have a greater affinity for a second part of the system than R$_F$. The system can include liquid/liquid systems, liquid/gas systems, liquid/solid systems, and/or gas/solid systems. Liquid/liquid systems, for example, can include systems having at least one liquid part that includes water and another liquid part that is hydrophobic relative to the part that includes water. Liquid/liquid systems can also include systems of which water is not a part of the system, such as hydrocarbon liquid systems. In exemplary embodiments, R$_F$ can be hydrophobic relative to Q$_s$ and/or Q$_s$ can be hydrophilic relative to R$_F$. R$_F$ can be hydrophobic and Q$_s$ can be hydrophilic, for example. The hydrophobic portion can be referred to as the tail of the R$_F$-surfactant, and the hydrophilic portion can be referred to as the head of the R$_F$-surfactant. The R$_F$-surfactants can include those surfactants having a tail or hydrophobic portion containing fluorine. The R$_F$-surfactant tail or hydrophobic portion can be referred to as an R$_F$ portion, and the R$_F$-surfactant head or hydrophilic portion can be referred to as a Q$_s$ portion. The R$_F$-surfactants can be produced from RF-intermediates utilizing the methods and systems detailed in published International Patent applications: PCT/US05/03429, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; PCT/US05/02617, entitled Compositions, Halogenated Compositions, Chemical Production and Telomerization Processes, filed Jan. 28, 2005; PCT/US05/03433, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; PCT/US05/03137, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005; and PCT/US05/03138, entitled Production Processes and Systems, Compositions, Surfactants, Monomer Units, Metal Complexes, Phosphate Esters, Glycols, Aqueous Film Forming Foams, and Foam Stabilizers, filed Jan. 28, 2005. Exemplary R$_F$-surfactants include those in Table 5 below.

TABLE 5

R$_F$-Surfactants

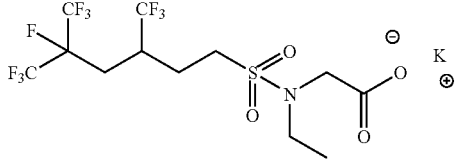
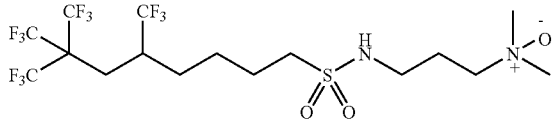
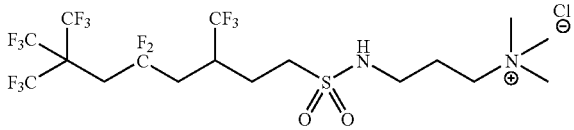
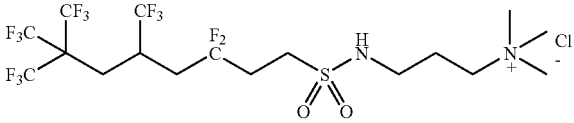
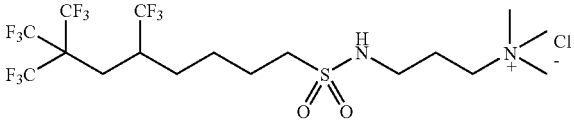
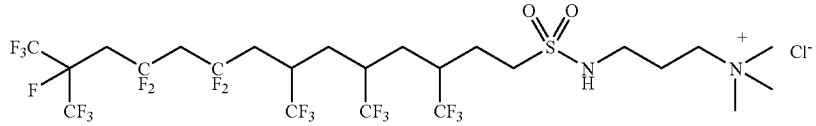

TABLE 5-continued

R$_F$-Surfactants

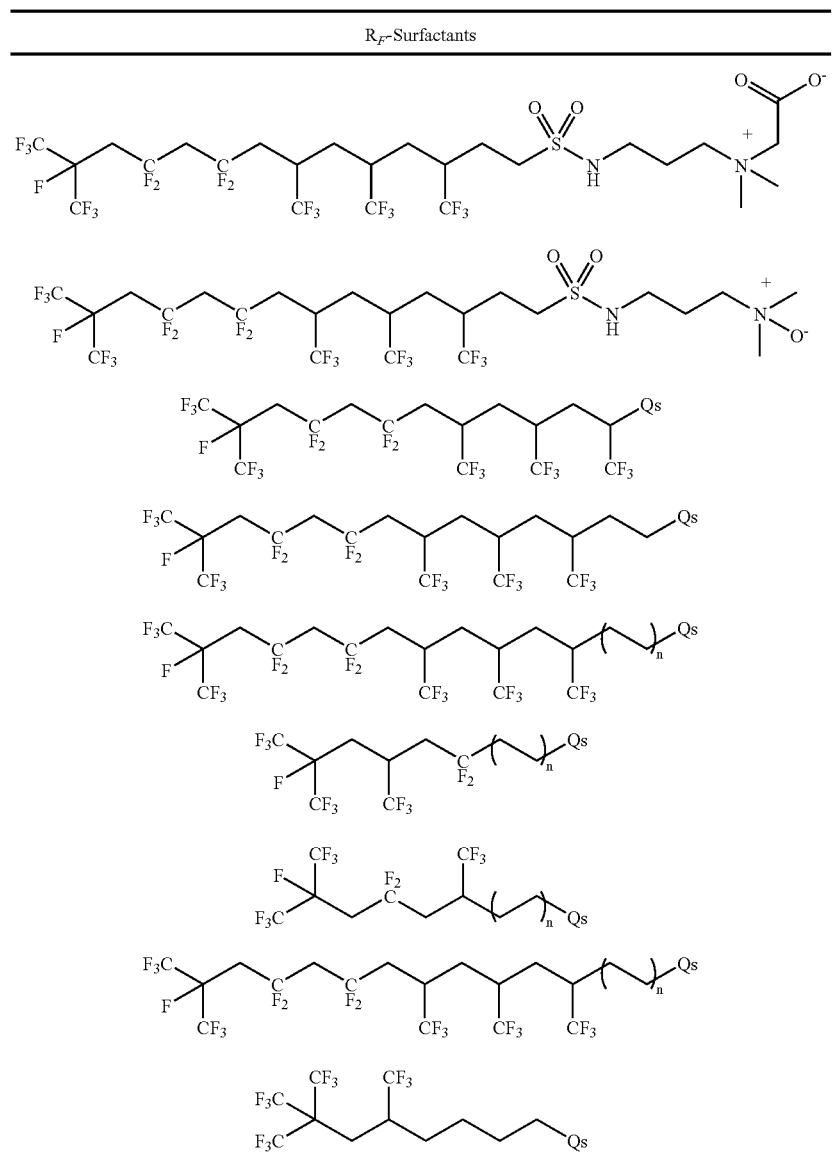

Where LC/MS can be used to identify compounds, Table 6 of LC/MS parameters, below, can be used

TABLE 6

LC-MS Parameters

| | |
|---|---|
| Column Type: | Phenomonex Luna C18 column, 5 micrometer |
| Column Size: | 2 x 50 mm |
| Column Temp: | 25° C. |
| Gradient Pump | Agilent 1100 Quat Pump G1311A |
| Detector: | Agilent Diode Array Detector G13115B |
| Detector Wavelength: | 250 nm (referenced against 360 nm) |
| Mass Detector: | Agilent 1100 MSD G1946C |
| Source: | Electrospray Positive Ion |
| Fragmentor: | 80 |
| Software | ChemStation Rev A.08.03 |
| Conc: | Ca 100 ppm |
| Injector:Rheodyne | 10 microliter |
| Elution Type: | Gradient |
| Flow Rate: | 0.3 mL/min |
| Mobile Phase: | A: Water (JT Baker HPLC grade) w/ 0.05% HCO$_2$H |

TABLE 6-continued

LC-MS Parameters

| | |
|---|---|
| Gradient Conditions: | B: Acetonitrile w/ 0.05% HCO$_2$H<br>90:10 A:B increase to 100% B in 6 min and then hold for 4 min at 100% B |

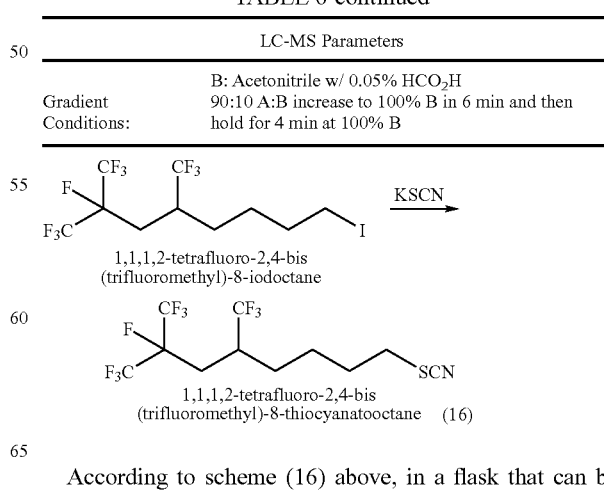

According to scheme (16) above, in a flask that can be equipped with an agitator, thermocouple and a reflux condenser, 30 grams (67 mmol) of 1,1,1,2-tetrafluoro-2,4-bis (trifluoromethyl)-8-iodooctane (see, e.g. Published International Patent Applications), 35 ml of absolute ethanol, 9.8 grams of potassium thiocyanate (KSCN) and 1.4 ml of glacial acetic acid (HOAc) can be placed to form a mixture. The mixture can be heated to reflux (about 84.7 C) and maintained for overnight while stirring. The mixture can be observed as a light yellow slurry and can be concentrated in vacuo to afford a viscous yellow slurry. The slurry cab be extracted with 300 mL of diethyl ether, (decanted twice) and filtered to afford a wet cake and a filtrate. The wet cake can be washed with three 100 mL portions of diethyl ether wherein the collected washings can be combined with the filtrate and concentrated in vacuo to afford 25.28 grams (99.5% yield) of the 1,1,1,2-tetrafluoro-2,4-bis(trifluoromethyl)-8-thiocyanatooctane product that can be observed as a light yellow oil. The product structure can be confirmed by NMR and/or chromatographic analysis.

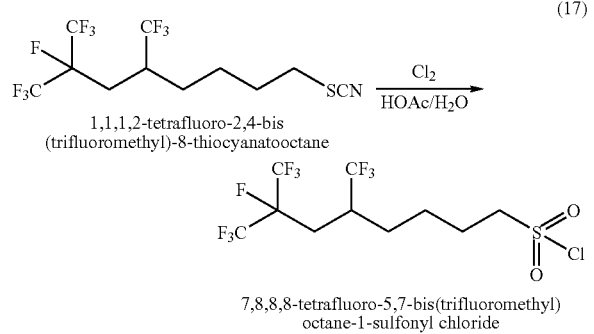

(17)

With reference to scheme (17) above, in a flask that can be equipped with an agitator, thermocouple, reflux condenser, and a chlorine gas dispersion tube, 25.2 grams (66.4 mmol) of 1,1,1,2-tetrafluoro-2,4-bis(trifluoromethyl)-8-thiocyanatooctane (refer to scheme (15) above) and 40 ml of glacial acetic acid (HOAc) can be placed to form a mixture and can be heated to about 60° C. The heated mixture can be sparged via a dispersion tube with chlorine gas (Cl₂) to form a reaction mixture for overnight. The reaction mixture can be cooled to about 10° C. and 50 ml of water added drop-wise. The reaction mixture can be warmed to RT and 200 ml of CHCl₃ and 100 ml of water added to form a multiphase mixture from which an organic phase can be separated from an aqueous phase. The aqueous phase can be collected and extracted with 200 ml of CHCl₃. The organic phases can be collected, combined and washed with three 300 ml portions of water and 300 ml of brine and then dried over Na₂SO₄, filtered and concentrated in vacuo to afford 26.26 grams (95.3% yield) of the 7,8,8,8-tetrafluoro-5,7-bis(trifluoromethyl)octane-1-sulfonyl chloride product that can be observed as a cloudy colorless oil. The product structure can be confirmed by NMR and/or chromatographic analysis.

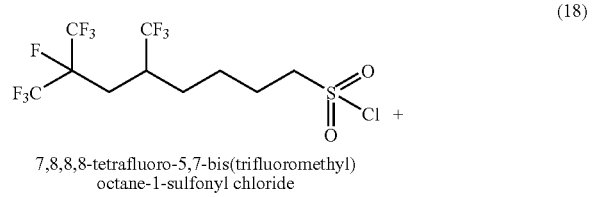

(18)

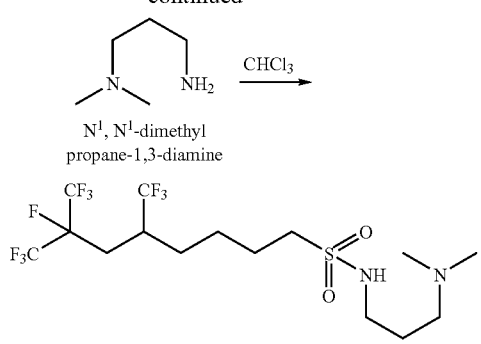

In accordance with scheme (18) above, in a flask that can be equipped with an agitator, thermocouple and a dry-ice/acetone bath, 17.80 grams (174.5 mmol) of N¹,N¹-dimethylpropane-1,3-diamine in 150 ml of CHCl₃ can be placed to form a mixture. To the mixture, 26.20 grams (62.3 mmol) of 7,8,8,8-tetrafluoro-5,7-bis(trifluoromethyl)octane-1-sulfonyl chloride (refer to scheme (16) above) and 150 ml of CHCl₃ can be added drop-wise over a 40 minute period to form a reaction mixture while maintaining the reaction temperature at between about 0° C. and −5° C. The reaction mixture can be allowed to warm to and maintained at RT while stirring for over the weekend. The reaction mixture can be washed by adding 300 ml of water, two 300 ml portions of bicarbonate, 300 ml of water, and 300 ml of brine wherein each step can be observed to afford a multiphase mixture from which an organic phase can be separated from an aqueous phase and the organic phase can be transferred to the next step. The washed organic phase can be dried over Na₂SO₄, filtered and concentrated in vacuo to afford 30.23 grams (99.8% yield) of the

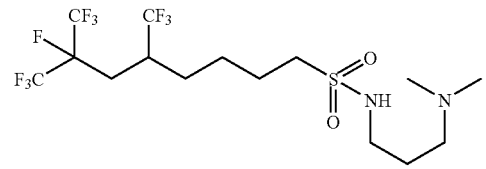

product that can be observed as a light yellow liquid. The product structure can be confirmed by NMR and/or chromatographic analysis.

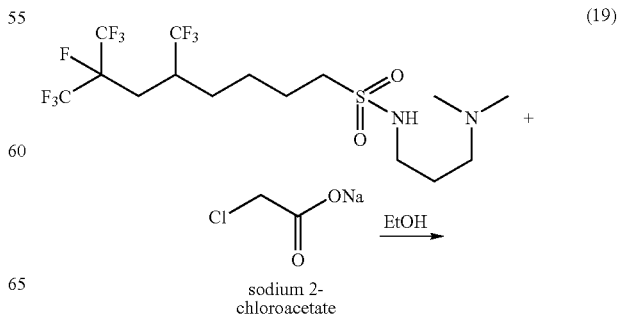

(19)

-continued

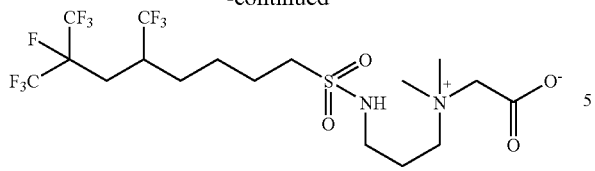

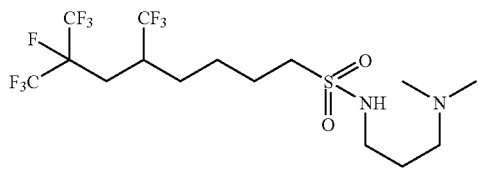

Referring to scheme (19) above, in a flask that can be equipped with an agitator, thermocouple and an addition funnel, A mixture of 10.0 grams (20.6 mmol) of

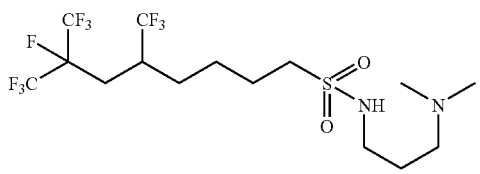

(refer to scheme (18) above), 50 ml of absolute ethanol (EtOH) and 2.40 grams (20.6 mmol) sodium chloroacetate can be placed to form a mixture. The mixture can be heated to reflux (about 79° C.) and stirred for a period of time to afford what can be observed as a thin white slurry. The slurry can be filtered and the filtrate concentrated in vacuo, dried at 45° C. under high vacuum to afford 11.29 grams of the

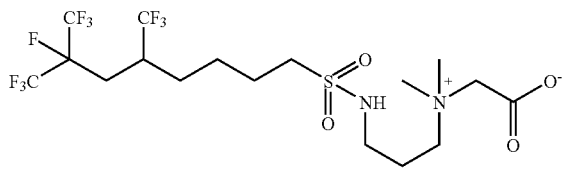

product that can be observed as a light yellow crunchy solid. The product structure can be confirmed by NMR and/or chromatographic analysis.

(20)

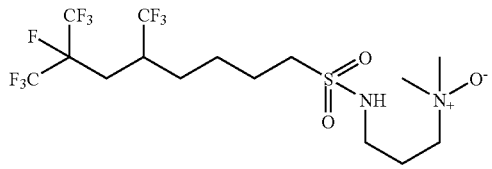

Referring to scheme (20) above, in a flask that can be equipped with an agitator, thermocouple, reflux condenser, and an addition funnel, 10.0 grams (20.6 mmol) of (refer to scheme (18) above), 20 ml of absolute ethanol (EtOH) and 3 ml of water can be placed to form a mixture. To the mixture, at RT, 9.6 ml of a 50% (wt/wt) $H_2O_2$ in water can be added drop-wise over a 5 minute period to form a reaction mixture. The reaction mixture can be heated to 35° C. and maintained for overnight. The reaction mixture can be treated portion-wise with 6 grams of decolorizing carbon (neutral) over a 2 hour period at 35° C. to form a slurry and heated to 50° C. and maintained stirring for overnight. A sample of the slurry can be collected and filtered and tested negative with KI/Starch paper for any unquenched peroxide. The remainder of the slurry can be filtered through celite and stripped of EtOH on a rotary evaporator. Trace EtOH can be removed by co-stripping three times with $CHCl_3$ to afford a concentrate. The concentrate can be concentrated in vacuo (2 hour under high vacuum at 45° C.) to afford 10.03 grams (97.4% yield) of the

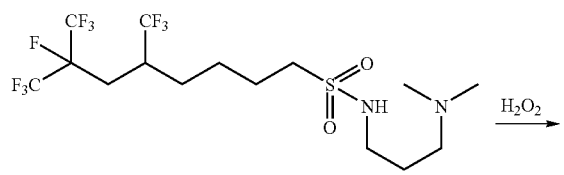

product that can be observed as an off-white crunchy solid. The product structure can be confirmed by NMR and/or chromatographic analysis.

(21)

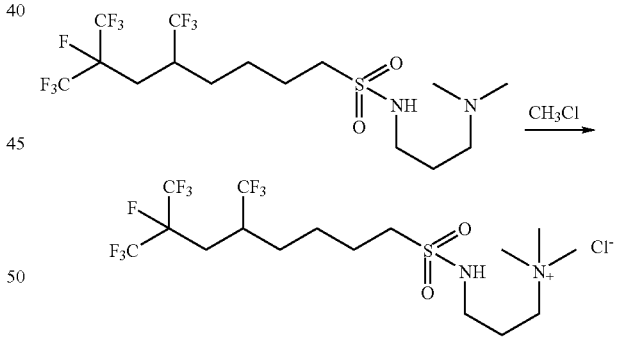

In conformity with scheme (21) above, in a sealable tube that can be equipped with an agitator and a thermocouple, 10.0 grams (20.6 mmol) of

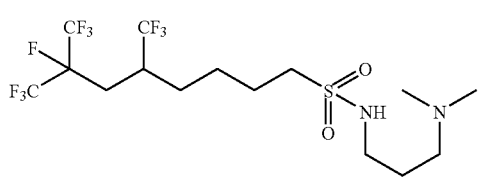

(refer to scheme (18) above), 2.1 grams (41.1 mmol) of chloromethane in 25 mL of methyl-tert-butyl ether (MTBE) can be placed to form a mixture and heated to 55° C. for an extended period of time. Stirring can be halted, the bottle cooled below about 0° C., vented, and the mixture concentrated in vacuo to afford 9.81 grams (88.9% yield) of the

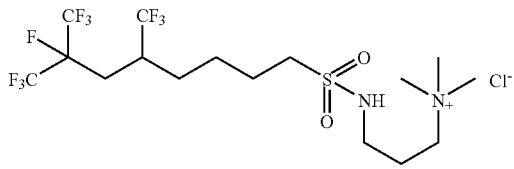

product that can be observed as a white waxy solid. The product structure can be confirmed by NMR and/or chromatographic analysis.

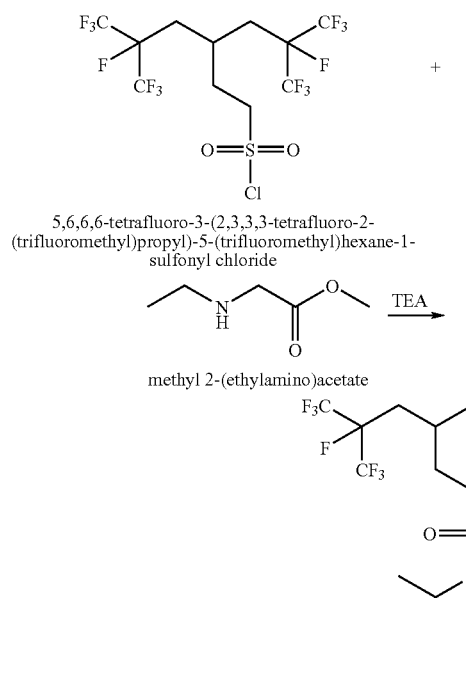

Referring to scheme (22) above, in a flask that can be equipped with an agitator, thermocouple, reflux condenser, and an addition funnel, 5 grams (0.01 mole) of 5,6,6,6-tetrafluoro-3-(2,3,3,3-tetrafluoro-2-(trifluoromethyl)propyl)-5-(trifluoromethyl)hexane-1-sulfonyl chloride (see, e.g. International Patent Applications), 1.2 grams (0.01 mole) of methyl 2-(ethylamino)acetate and 10 mL of chloroform can be placed to form a mixture and chilled to 0° C. To the mixture, 3 mL of triethylamine (TEA) and 10 mL of chloroform can be added drop wise to form a reaction mixture. The peak temperature during addition can be about 3.9° C. The reaction mixture can be allowed to warm to room temperature while stirring and maintained for overnight. To the reaction mixture, 20 mL of cholorform can be added and washed with two 25 mL portions a saturated solution NaHCO$_3$ in water, two 25 mL portions of water and 25 mL of a saturated NaCl solution in water to form multiphase mixtures from which an organic phase can be separated from an aqueous phase. The organic phase can be collected, dried and concentrated to form a concentrate. To the concentrate, 25 mL of chloroform can be added to form a diluant. To the diluant, 25 mL of a 5% (wt/wt) solution of HCl in water can be added to afford an acidified diluant. To the acidified diluant, 25 mL of a 1 N solution of NaOH can be added to form a neutral multiphase mixture from which an organic phase can be separated from an aqueous phase. The organic phase can be dried and concentrated to afford 3.45 grams of the

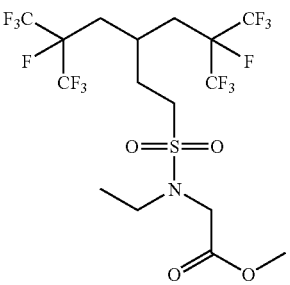

product that can be observed as a yellow oil (59.5% yd.). The product structure can be confirmed by NMR and/or chromatographic analysis.

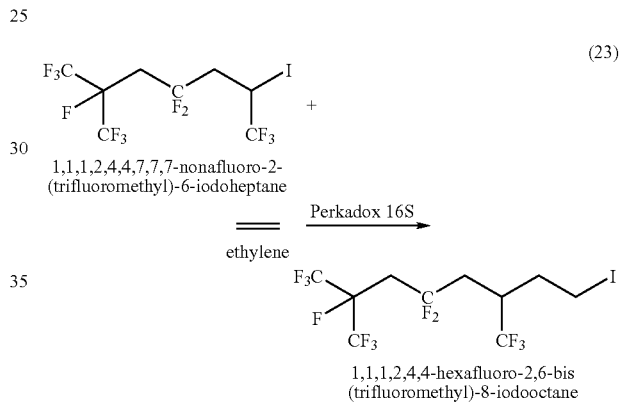

In reference to scheme (23) above, in a 60 mL reactor that can be equipped with an agitator, ethane delivery apparatus and a thermocouple, 23.0 grams (50.4 mmol) of 1,1,1,2,4,4,7,7,7-nonafluoro-2-(trifluoromethyl)-6-iodoheptane (see, e.g. Published Patent Applications) and 0.95 grams (2.5 mmol) of di-(t-butylcyclohexyl) peroxydicarbamate (Akzo Nobel—Perkadox 16S) can be placed to form a mixture. The reactor can be sealed and heated to about 50° C. while stirring. To the reactor, ethylene can be added in a continuous fashion to afford and maintain a reactor pressure of about 260 psig to form a reaction mixture. After about 2 hours, the ethylene feed and heating can be discontinued, the reaction cooled to about 10° C., the agitation stopped and the reactor vented and opened. To the reaction mixture, 1.0 gram of Perkadox 16S can be added and heating continued for 3 hours. To the reaction mixture, 0.9 gram of Perkadox 16S can be added, the reactor heated to about 50° C., pressurized with ethylene to about 260 psig and maintained for about 5 hours. To the reaction mixture, additional Perkadox 16S can be added and the above reaction conditions established and maintained for overnight. The reaction mixture can be collected and placed on a Kugelrohr distillation apparatus to afford 26.05 grams of the 1,1,1,2,4,4-hexafluoro-2,6-bis(trifluoromethyl)-8-iodooctane product. The product structure can be confirmed by NMR and/or chromatographic analysis.

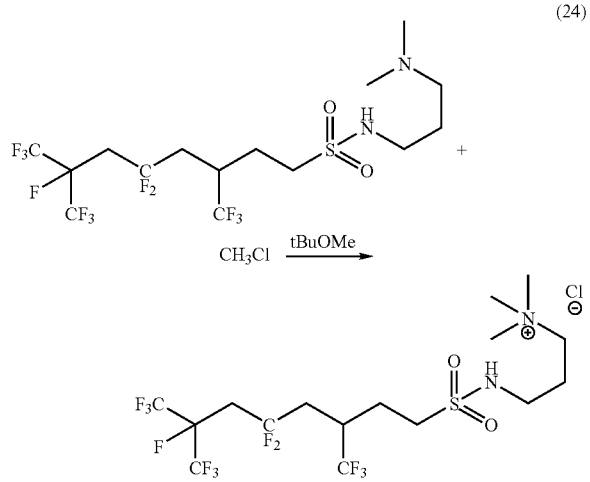

Conforming to scheme (24) above, in a sealable tube that can be equipped with an agitator, thermocouple, reflux condenser, and an addition funnel, 6.0 grams (11.5 mmol) of (see, e.g. Published International Patent Applications) and 1.2 grams (23 mmol) of chloromethane (CH$_3$Cl) in 30 mL of methyl-tert-butyl ether (tBuOMe) can be placed to form a mixture and heated to about 55° C. for an extended period of time. A thick layer can be observed to have settled on the bottom of the tube restricting the stirring. The tube can be cooled and vented, and heated to regain homogeneity. The stir bar can be replaced with a different type and the contents were cooled and charged with an additional 2.9 grams of CH$_3$Cl. Once sealed, the heating can be resumed. A thick layer can be observed to have settled out again. The tube can be sonicated to homogenize and stirred at 55° C. for overnight. The tube can be cooled below about 0° C. and vented where the contents of the tube can be observed as a multiphase mixture wherein a liquid phase can be separated from a clear orange tar. The liquid phase can be discarded and ether added and the contents heated and sonicated to dissolve. The contents can be cooled to RT and the ether decanted from the tar that can be observed to have reformed (precipitated). The tar can be dissolved in dichloromethane, transferred and concentrated to afford to 5.41 grams (90.0% yield) of the product that can be observed as an orange semi-solid. The product structure can be confirmed by NMR and/or chromatographic analysis.

In reference to scheme (25) above, in a reactor that can be equipped with an agitator, thermocouple, and an ethylene addition apparatus, 23 grams (50.4 mmol) of 1,1,1,2,6,6-hexafluoro-2,4-bis (trifluoromethyl)-6-iodohexane (see, e.g. Published Patent Applications) and 0.95 grams (2.5 mmol) of di-(t-butylcyclohexyl) peroxydicarbamate (Akzo Nobel—Perkadox 16S) can be added to form a mixture. The reactor can be sealed, heated to 50° C. while stirring and continuously pressurized to about 260 psig with ethylene (reactions conditions) to form a reaction mixture. After 2 hours, the ethylene feed and heating can be discontinued, the reaction cooled to about 10° C., the agitation can be discontinued and the reactor vented and opened. To the reaction mixture, 1.0 grams of the Perkadox 16S can be added, reaction conditions restored and maintained for over a weekend. To the reaction mixture, 0.9 grams of Perkadox 16S can be added and the reaction conditions restored and maintained for from about 5 hours 24 hours wherein additional Perkadox 16S can be added. The reaction mixture can be collected and placed on a Kugelrohr distillation apparatus to 26.05 grams of the 1,1,1, 2,6,6-hexafluoro-2,4-bis(trifluoromethyl)-8-iodooctane product. The product structure can be confirmed by NMR and/or chromatographic analysis.

Referring to scheme (26) above, in a sealable tube that can be equipped with an agitator and a thermocouple, 7.1 grams (13.6 mmol) 3,3,7,8,8,8-hexafluoro-5,7-bis(trifluoromethyl) octane-1-sulfonic acid (3-dimethylaminopropyl)amide (see, e.g. Published Patent Applications) and 1.4 grams (27.2 mmol) of chloromethane and 30 mL of methyl-tert-butyl ether can be placed to form a mixture. The mixture can be heated to 55° C. and maintained for an extended period of time. A thick layer can be observed to have settled on the bottom of the tube thereby restricting the stirring. The tube can be cooled and vented and heated to regain homogeneity. The agitator can be replaced with a different type and the contents cooled and charged with an additional 3.1 grams of CH$_3$Cl. The tube can be sealed and the heating resumed. A layer can be observed to have settled out again. The tube can be sonicated to homogenize and stirred at 55° C. for overnight to form a multiphase mixture from which a liquid phase can be separated from a tar phase. The tube can be cooled to below about 0° C., vented and the liquid decanted from the tar. To the tar, ether can be added and the contents heated and sonicated to dissolve. The mixture can be cooled to RT and the liquid decanted from the tar that can be observed to have reformed. The tar can be dissolved in dichloromethane, transferred and concentrated to afford 7.0 grams (90.0% yield) of the 3,3,7, 8,8,8-hexafluoro-5,7-bis(trifluoromethyl)octane-1-sulfonic acid (3-trimethylaminopropyl)amido chloride product that can be observed as an orange semi-solid. The product structure can be confirmed by NMR and/or chromatographic analysis.

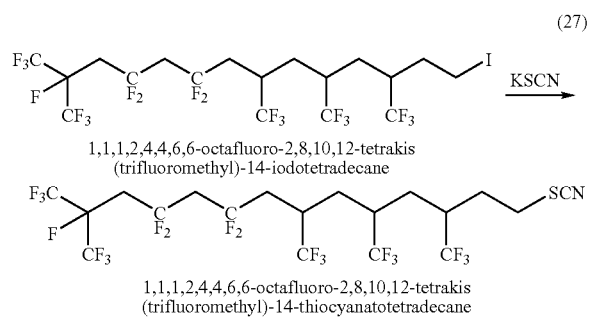

(27)

1,1,1,2,4,4,6,6-octafluoro-2,8,10,12-tetrakis (trifluoromethyl)-14-iodotetradecane 1,1,1,2,4,4,6,6-octafluoro-2,8,10,12-tetrakis (trifluoromethyl)-14-thiocyanatotetradecane According to scheme (27) above, in a flask that can be equipped with an agitator, thermocouple and a reflux condenser, 20 grams (27 mmol) of 1,1,1,2,4,4,6,6-octafluoro-2, 8,10,12-tetrakis(trifluoromethyl)-14-iodotetradecane (see, e.g. Published Patent Applications), 20 ml of absolute ethanol, 3.9 grams (40.5 mmol) of potassium thiocyanate (KSCN) and 0.5 ml of glacial acetic acid (HOAc) can be placed to form a mixture. The mixture can be heated to reflux (84.7 C) and maintained stirring for overnight. The mixture can be concentrated in vacuo to afford what can be observed as a thick yellow slurry. The slurry can be extracted with 300 ml of diethyl ether and decanted twice and filtered to afford a wet cake and a filtrate. The wet cake can be washed with three 100 ml portions of diethyl ether and the filtrates combined. The combined filtrates can be concentrated in vacuo to afford 17.12 grams (94.6% yield) of the 1,1,1,2,4,4,6,6-octafluoro-2,8,10,12-tetrakis(trifluoromethyl)-14-thiocyanatotetradecane product that can be observed as a light yellow oil. The product structure can be confirmed by NMR and/or chromatographic analysis.

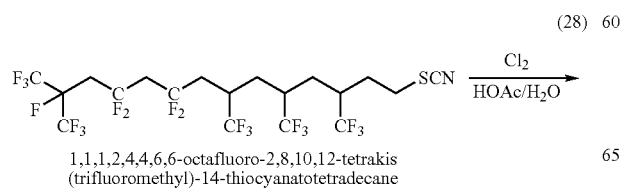

(28)

1,1,1,2,4,4,6,6-octafluoro-2,8,10,12-tetrakis (trifluoromethyl)-14-thiocyanatotetradecane

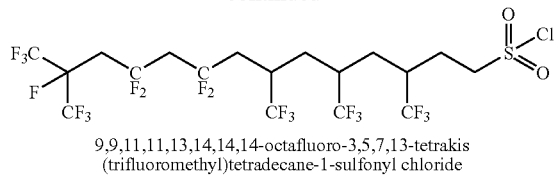

9,9,11,11,13,14,14,14-octafluoro-3,5,7,13-tetrakis (trifluoromethyl)tetradecane-1-sulfonyl chloride Referring to scheme (28) above, in a flask that can be equipped with an agitator, thermocouple, reflux condenser, and a dispersion tube, A yellow solution of 17.1 grams (25.5 mmol) of 1,1,1,2,4,4,6,6-octafluoro-2,8,10,12-tetrakis(trifluoromethyl)-14-thiocyanatotetradecane (refer to scheme (23) above) and 30 ml of HOAc can be placed to form a mixture. The mixture can be heated to about 60° C. and sparged via the dispersion tube with chlorine gas (Cl$_2$) for overnight. The flow of chlorine can be observed to have stopped overnight, causing the reaction material to back up into the trap. A portion of the mixture, what can be observed as a white liquid, can remain in the flask and can still be in contact with the thermocouple. Chlorination can be continued for about two overnight periods to afford what can be observed as a slurry. The slurry can be cooled to about 10° C. and about 40 ml of water can be added drop wise to form a reaction mixture. The reaction mixture can be warmed to room temperature (RT) and diluted with about 200 ml of chloroform (CHCl$_3$) and about 100 ml of water to form a multiphase mixture from which an organic phase can be separated from an aqueous phase. The aqueous phase can be extracted with 200 ml of CHCl$_3$ and the organic phases combined. The combined extracts can be washed with three 300 mL portions of water and the organic phase collected. The organic phase can be washed with 300 ml of brine and dried over Na$_2$SO$_4$, filtered and concentrated in vacuo to afford 16.52 grams (91.0% yield) of the 9,9,11,11,13,14,14,14-octafluoro-3,5,7,13-tetrakis(trifluoromethyl)tetradecane-1-sulfonyl chloride that can be observed as a cloudy colorless oil. The product structure can be confirmed by NMR and/or chromatographic analysis.

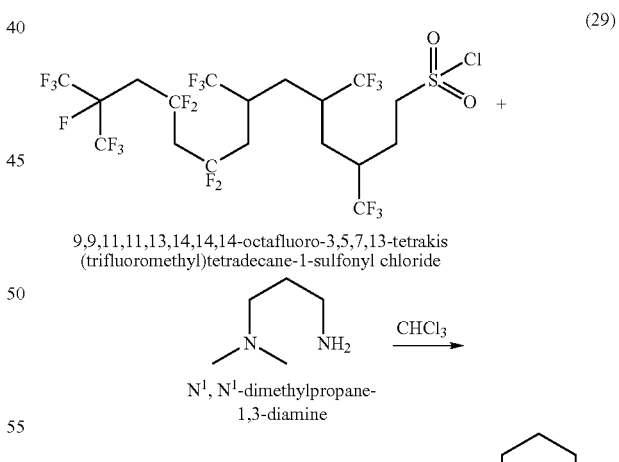

(29)

9,9,11,11,13,14,14,14-octafluoro-3,5,7,13-tetrakis (trifluoromethyl)tetradecane-1-sulfonyl chloride N$^1$, N$^1$-dimethylpropane-1,3-diamine

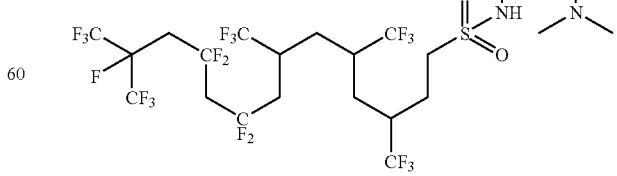

In reference to scheme (29) above, in a flask that can be equipped with an agitator, thermocouple, reflux condenser, addition funnel and a dry-ice/acetone bath, 16.5 grams (23.1 mmol) of 9,9,11,11,13,14,14,14-octafluoro-3,5,7,13-tetrakis(trifluoromethyl)tetradecane-1-sulfonyl chloride (refer to scheme (24) above) and 50 mL of CHCl$_3$ can be placed to form a mixture. In the addition funnel, 6.60 grams (64.9 mmol) of 3-dimethylaminopropylamine and 50 ml of CHCl$_3$ can be added to form an addition mixture. To the mixture, the addition mixture can be added drop-wise over a 30 minute period to form a reaction mixture while maintaining the temperature at between about 0° C. and −5° C. The reaction mixture can be allowed to warm to room temperature (RT) and stir overnight. The reaction mixture can be washed with one 200 ml portion of water, two 200 ml portions of a saturated solution of bicarbonate and one 200 ml portion of brine wherein each step can be observed to form a multiphase mixture from which an organic phase can be separated from an aqueous phase. The organic phase can be collected and dried over Na$_2$SO$_4$, filtered and concentrated in vacuo to afford 39.30 grams (95.9% yield) of the

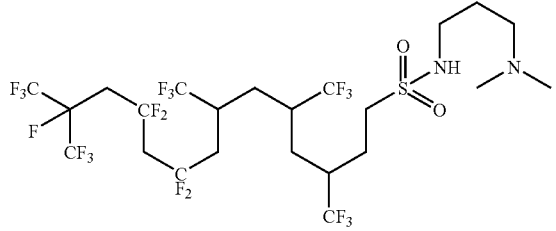

product that can be observed as a light yellow liquid. The product structure can be confirmed by NMR and/or chromatographic analysis.

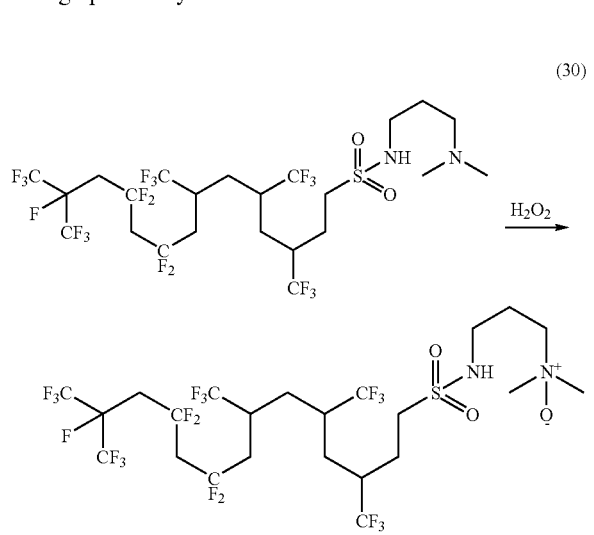

According to scheme (30) above, in a flask that can be equipped with an agitator, thermocouple, reflux condenser, and an addition funnel, 5.80 grams of

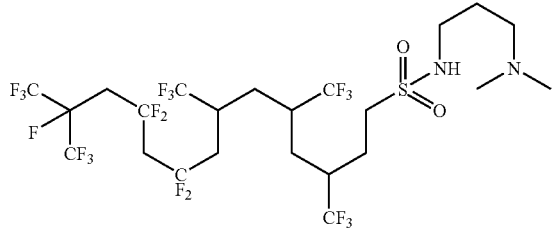

(refer to scheme (26) above), 15 ml of absolute ethanol and 1.1 ml of water at RT can be placed to form a mixture. To the mixture, 3.5 ml of 50% H$_2$O$_2$ can be added drop-wise over a 1 minute period to form a reaction mixture. The reaction mixture can be heated to 35° C. and maintained for over the weekend. The reaction mixture can be treated portion-wise with 5 grams of decolorizing carbon (neutral) over a 1 hour period at 35° C. to form a slurry. The slurry can be heated to about 50° C. and maintained for overnight while stirring.

A sample of the slurry can be filtered and the filtrate tested negative for the presence of peroxides. The remainder of the slurry can be filtered through celite to afford a filtrate. The filtrate can be concentrated in vacuo to afford the

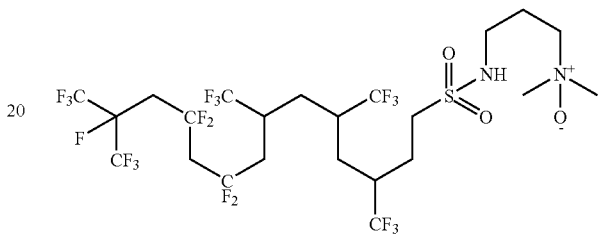

product that can be observed as an off-white crunchy solid. The product structure can be confirmed by NMR and/or chromatographic analysis.

(30)

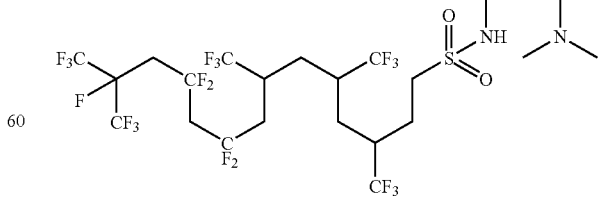

In accordance with scheme (31) above, in a sealable tube that can be equipped with an agitator, 5.50 grams (7.1 mmol) of (refer to scheme (26) above), 2.2 grams of chloromethane in 20 mL of methyl-tert-butyl ether (MTBE) can be placed to form a mixture and heated to about 55° C. for an extended period of time. Stirring can be halted and the mixture cooled to below about 0° C. and the tube vented. The mixture can be concentrated in vacuo to afford the

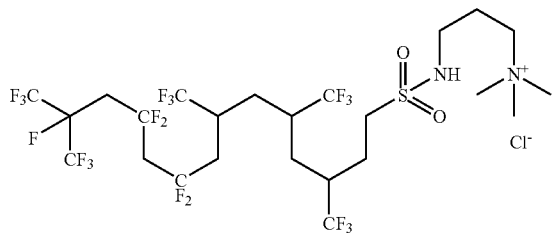

product that can be observed as a white waxy solid. The product structure can be confirmed by NMR and/or chromatographic analysis.

(32)

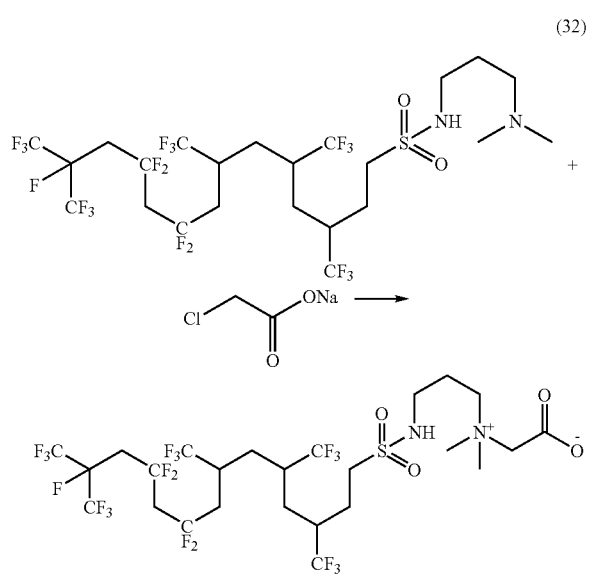

In accordance with scheme (32) above, in a flask that can be equipped with an agitator, thermocouple, reflux condenser, and an addition funnel, 5.50 grams (7.1 mmol) of

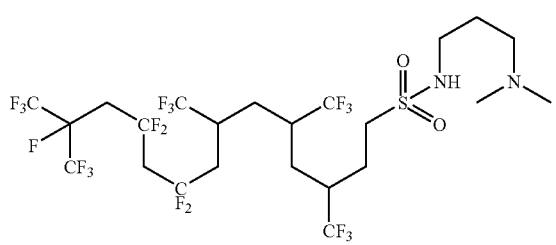

(refer to scheme (26) above), 20 mL of absolute ethanol and 0.90 grams (7.1 mmol) of sodium chloroacetate can be placed to form a mixture. The mixture can be heated to reflux (about 79° C.) and stirred for a period of about 6.5 days. The reaction mixture can be observed as a thin white slurry and can be filtered to afford a filtrate. The filtrate can be concentrated in vacuo and dried at 45° C. under high vacuum to afford 11.03 grams of the

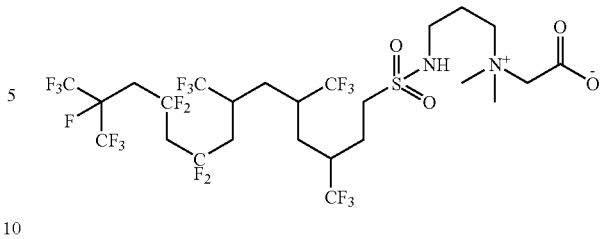

product that can be observed as a light yellow crunchy solid. The product structure can be confirmed by NMR and/or chromatographic analysis.

According to another embodiment, a mercaptan $R_F$-intermediate may also be produced by reacting a iodine $R_F$-intermediate with thiourea to make the isothiuronium salt and treating the isothiuronium salt with sodium hydroxide to give the mercaptan $R_F$-intermediate plus sodium iodide, as described in U.S. Pat. No. 3,544,663 herein incorporated by reference.

In an exemplary aspect of the disclosure, the mercaptan $R_F$-intermediate may be attached to a Qs portion such as group 2-acrylamido-2-methyl-1 propane sulfonic acid available from Lubrizol as AMPS 2403, as generally described in U.S. Pat. No. 4,000,188 herein incorporated by reference.

Aminoxides of the $R_F$-surfactants can be produced according to processes that include those generally described in U.S. Pat. No. 4,983,769, herein incorporated by reference. Accordingly, sulfoamidoamines can be combined with ethanol and water and 70% (wt/wt) hydrogen peroxide and heated to at least 35° C. for 24 hours. Activated carbon can be added and the mixture and refluxed for about 2 hours. The reaction mixture can be filtered and the filtrate evaporated to dryness to provide the amine oxide of the $R_F$-surfactant.

In accordance with another embodiment of the disclosure, processes are provided that can be used to alter the surface tension of a part of a system having at least two parts. The system can include liquid/solid systems, liquid/gas systems, gas/solid systems, and/or liquid/liquid systems. In an exemplary embodiment, the liquid/liquid systems can have one part that includes water and another part that includes a liquid that is relatively hydrophobic when compared to water. According to another example, the liquid/liquid system can contain one part that is relatively hydrophobic when compared to water and/or relatively hydrophobic when compared to another part of the system. $R_F$-surfactants can be used to alter the surface tension of a part of the system, for example, by adding the $R_F$-surfactant to the system.

$R_F$-surfactants may be used as relatively pure solutions or as mixtures with other components. For example, and by way of example only, the $R_F$-surfactants can be added to a system and the surface tension of the system determined by the Wilhelmy plate method and/or using the Kruss Tensiometer method.

As another example, the surface tensions of

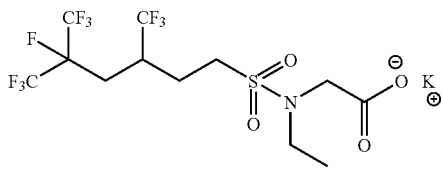

at various concentrations can be determined and the data as indicated in Plot # 1 as shown in FIG. 3.

As another example, the surface tensions of

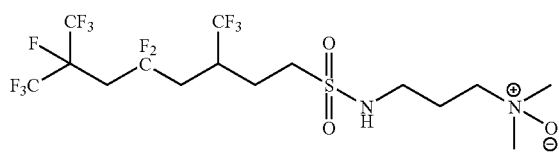

at various concentrations can be determined and the data as indicated in Plot # 2 as shown in FIG. 4.

As another example, the surface tensions of

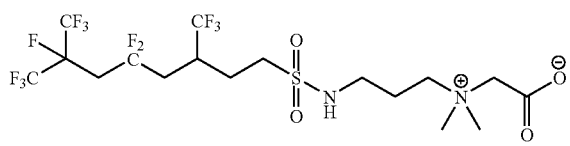

at various concentrations can be determined and the data as indicated in Plot # 3 as shown in FIG. 5.

As another example, the surface tensions of

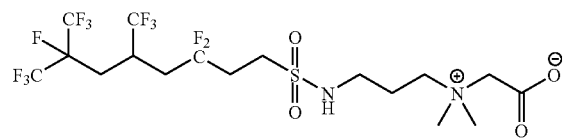

at various concentrations can be determined and the data as indicated in Plot # 4 as shown in FIG. 6.

As another example, the surface tensions of

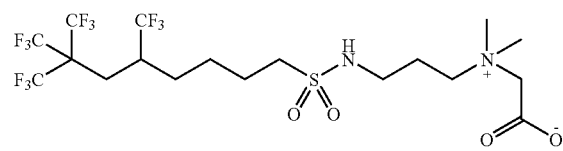

at various concentrations can be determined and the data as indicated in Plot # 5 as shown in FIG. 7.

As another example, the surface tensions of

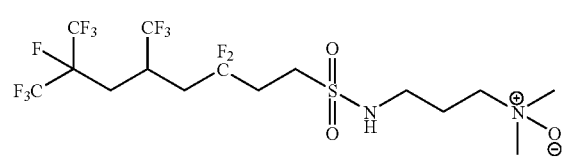

at various concentrations can be determined and the data as indicated in Plot # 6 as shown in FIG. 8.

As another example, the surface tensions of

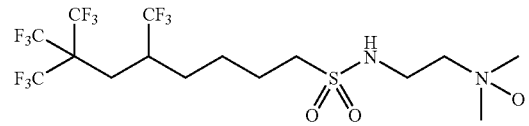

at various concentrations can be determined and the data as indicated in Plot # 7 as shown in FIG. 9.

As another example, the surface tensions of

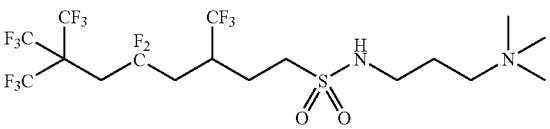

at various concentrations can be determined and the data as indicated in Plot # 8 as shown in FIG. 10.

As another example, the surface tensions of

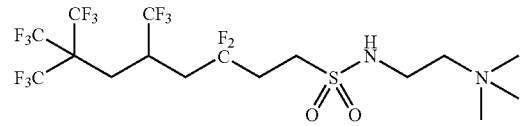

at various concentrations can be determined and the data as indicated in Plot # 9 as shown in FIG. 11.

As another example, the surface tensions of

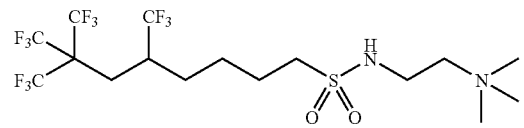

at various concentrations can be determined and the data as indicated in Plot # 10 as shown in FIG. 12.

As another example, the surface tensions of

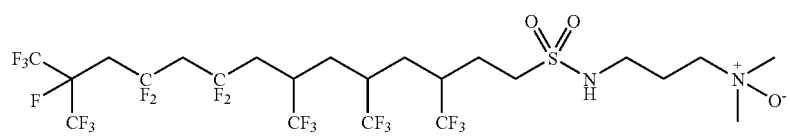

at various concentrations can be determined and the data as indicated in Plot # 11 as shown in FIG. 13.

As another example, the surface tensions of

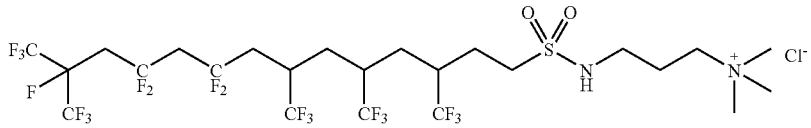

at various concentrations can be determined and the data as indicated in Plot # 12 as shown in FIG. 14.

As another example, the surface tensions of

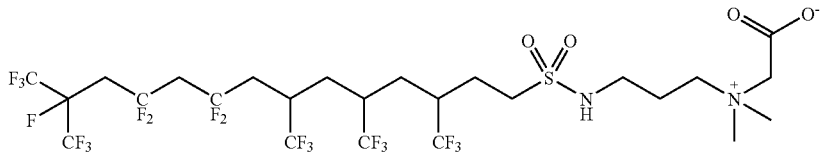

various concentrations can be determined and the data as indicated in Plot # 13 as shown in FIG. 15.

$R_F$-surfactants described above may be incorporated into detergents, emulsifiers, paints, adhesives, inks, wetting agents, foamers, and/or defoamers, for example.

$R_F$-surfactants can be incorporated into AFFF formulations and these formulations can be used as fire-fighting foams, to prevent, and/or extinguish combustion. An exemplary use of AFFFs that include an $R_F$-surfactant includes the addition of the AFFF to high pressure misting systems, the misting systems being used to prevent and/or extinguish combustion. AFFF formulations can be provided to a substrate, for example. The substrate can include liquid and/or solid compositions. The AFFF formulations can also be dispersed into an atmosphere including gaseous atmospheres, such air to prevent and/or extinguish combustion.

The formulations can include other components such as water soluble solvents. These solvents may facilitate the solubilization of the $R_F$-surfactants and other surfactants. These solvents can also act as foam stabilizers and/or freeze protection agents. Exemplary solvents can include ethylene glycol, diethylene glycol, glycerol, ethyl Cellusolve®, butyl Carbitol®, Dowanol DPM®, Dowanol TPM®, Dowanol PTB®, propylene glycol, and/or hexylene glycol. Additional components to the formulation, such as polymeric stabilizers and thickeners, can be incorporated into the formulation to enhance the foam stability property of a foam produced from aeration of the aqueous solution of the formulation. Exemplary polymeric stabilizers and thickeners include partially hydrolyzed protein, starches, polyvinyl resins such as polyvinyl alcohol, polyacrylamides, carboxyvinyl polymers, and/or poly(oxyethylene)glycol. Polysaccharide resins, such as xanthan gum, can be included in the formulation as a foam stabilizer in formulations for use in preventing or extinguishing polar solvent combustion, such as alcohol, ketone, and/or ether combustion, for example. The formulation can also include a buffer to regulate the pH of the formulation, for example, tris(2-hydroxyethyl)amine or sodium acetate, and a corrosion inhibitor such as toluoltriazole or sodium nitrite may be included. Water soluble electrolytes such as magnesium sulphate may be included and can improve film-spreading characteristics of the formulation.

The $R_F$-surfactants can also be useful in formulations that include other surfactants such as alkyl sulfate, alkylethersulfates, alphaolefinsulfonates, alkyl sulfobetaines, alkyl polyglycerides, alkylamidopropylbetaines, alkylimidazolinedicarboxylates, 2-alkylthiopropionamido-2 methylpropanesulfonoic acid sodium salt, alkyliminodipropinates, alkylsulfonates, ethoxylated alkylphenols, dialkylsulfosuccinates, and/or alkyltrimethyl ammonium chloride.

A variation of AFFF, ARAFFF, an acronym for Alcohol Resistant Aqueous Film Forming Foam(s), can be used to extinguish hydrocarbon fires in much the same manner that AFFF foams are used and may also be used to extinguish fires involving water soluble solvents such as acetone and isopropanol which conventional AFFF foams will not extinguish.

ARAFFF formulations can contain the same ingredients as conventional AFFF formulations plus a polysaccharide such as xanthan gum and, in some formulations, a polymeric foam stabilizer. Polymeric foam stabilizers are offered by DuPont® and Dynax®, Inc. An exemplary DuPont product, Forafac® 1268, is a water soluble acrylic polymer. An exemplary Dynax product, DX5011®, is an ethyleneimine polymer. Xanthan gum is offered by several suppliers, including Kelco CP (Kelzan) and Rhodia North America (Rhodopol).

Polysaccharide alone can be sufficient to make ARAFFF formulations alcohol resistant, but the amount required produces a foam concentrate that can be quite viscous. The use of a polymeric foam stabilizer can permit a reduction in the amount of polysaccharide required to give useful alcohol resistance.

Because of the possibility of microbial attack on polysaccharide solutions, ARAFFF concentrates can contain an effective amount of a biocide such as Kathon CG ICP, manufactured by Rohm & Haas. Many other biocides such as Acticide, Nipacide and Dowicil can also be effective.

Some ARAFFF formulations can be designed to be proportioned at different percentages depending on whether the substrate to be extinguished is a hydrocarbon or an alcohol type substrate, for example. Alcohol type can include any fuel having a hydroxyl group.

Exemplary ARAFFF formulations utilizing the $R_F$ surfactants can be provided and/or formulated in accordance with the methods described in the Published International Applications. Foam stabilizers, such as $R_F$-stabilizers that include $R_F$ groups described above, for example, can be prepared. $R_F$-stabilizers can include $R_F$-$Q_{FS}$ compositions. Example foam stabilizer compositions can include $R_F(R_T)_nQ_{FS}$. The $R_F$ group can comprise at least one —$CF_3$ group. The $R_T$ group can comprise —$CF_2CH_2CH(CF_3)$—, with n being at least 1. The $Q_{FS}$ group can be at least one atom of the periodic table of elements, wherein at least a portion of the $R_F$ and $R_T$ groups are hydrophobic relative to the $Q_{FS}$ group, and at least a portion of the $Q_{FS}$ group is hydrophilic relative to the $R_F$ and $R_T$ groups.

According to exemplary embodiments the $R_F$ portion can at least partially include an $R_F(R_T)$n portion as described above. The $R_F(R_T)$n portion of the surfactant can also include the $R_S$ portion described above. In accordance with exemplary implementations the $R_S$ portion can be incorporated to provide additional carbon between the $R_F$ and/or $R_F(R_T)$n portions and the $Q_{FS}$ portion of the surfactant. Exemplary $R_s$ portions include —$CH_2$—$CH_2$—$Q_{FS}$ can include portions that have a greater hydrophilic character than $R_F$. Exemplary $Q_{FS}$ portions include the Qs portions described herein as well as those having polyalkoxylated amines. Exemplary $R_F$-Foam Stabilizers include, but are not limited to those in Table 7 below.

TABLE 7

Exemplary $R_F$-Foam Stabilizers

[chemical structures]

$R_F$-metal complexes such as $R_F$-$Q_{MC}$ incorporating the $R_F$ portions are also provided. The $R_F$ portions can be incorporated as acid halides or carboxylic acids, for example, with the acid halide including, but not limited to, acid fluorides, for example. According to exemplary embodiments the $R_F$ portion can at least partially include an $R_F(R_T)$n portion as described above. The $R_F(R_T)$n portion of the complex can also include the $R_S$ portion described above. In accordance with exemplary implementations the $R_S$ portion can be incorporated to provide additional carbon between the $R_F$. and/or $R_F(R_T)$n portions and the $Q_{MC}$ portion of the complex. Exemplary $R_s$ portions include —$CH_2$—$CH_2$—. $R_F$-metal complexes can include $R_F$-intermediates and, as such, $Q_g$ can be interchangeable with $Q_{MC}$. $Q_{MC}$ can include the portion of a ligand of a metal complex that is coordinated with the complexed metal, for example. Metal complexes are provided that can include $R_F(R_T)_n Q_{MC}$. The $R_F$ group can include at least one —$CF_3$ group. The $R_T$ group can include —$CF_2CH_2CH$ ($CF_3$)—, with n being at least 1. The $Q_{MC}$ group can include a charged group configured to complex one or more metal ions. Exemplary $R_F$-metal complexes include, but are not limited to, those in Table 8 below.

TABLE 8

Exemplary $R_F$-Metal Complexes

[chemical structures]

$R_F$-metal complexes such as $R_F$-$Q_{MC}$ incorporating the $R_F$ portions are also provided. The $R_F$ portions can be incorporated as acid halides or carboxylic acids, for example, with the acid halide including, but not limited to, acid fluorides, for example. According to exemplary embodiments the $R_F$ portion can at least partially include an $R_F(R_T)$n portion as described above. The $R_F(R_T)$n portion of the complex can also include the $R_S$ portion described above. In accordance with exemplary implementations the $R_S$ portion can be incorporated to provide additional carbon between the $R_F$ and/or $R_F(R_T)$n portions and the $Q_{MC}$ portion of the complex. Exemplary $R_s$ portions include —$CH_2$—$CH_2$—. $R_F$-metal complexes can include $R_F$-intermediates and, as such, $Q_g$ can be interchangeable with $Q_{MC}$. $Q_{MC}$ can include the portion of a ligand of a metal complex that is coordinated with the complexed metal, for example. Exemplary $R_F$-metal complexes can be prepared by way of the following exemplary synthetic steps.

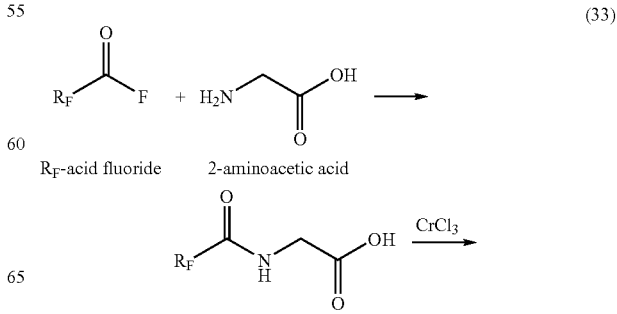

(33)

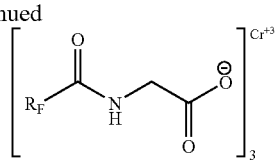

An acid fluoride $R_F$-intermediate can be reacted with an amino acid such as glycine (2-aminoacetic acid) to produce an amido-carboxylic acid. The amido-carboxylic acid can be reacted with chromic chloride in an alcohol such as methanol and/or isopropanol to produce an exemplary $R_F$-metal complex such as a $R_F$ chrome complex. Exemplary acid $R_F$-intermediates for use in preparation of $R_F$-metal complexes can include ethylene carboxylic acid $R_F$-intermediates and/or mixtures of ethylene carboxylic acid $R_F$-intermediates and carboxylic acid $R_F$-intermediates. Exemplary preparations can be performed in accordance with U.S. Pat. Nos. 3,351,643, 3,574,518, 3,907,576, 6,525,127 and 6,294,107, herein incorporated by reference. $R_F$-metal complexes can include a ligand having a $R_F$ portion and a $Q_{MC}$ portion associated with the metal of the complex. In exemplary embodiments the $Q_{MC}$ portion can have a greater affinity for the metal complex than the $R_F$ portion. $R_F$-metal complexes can be used to treat substrates such as paper, leather, textiles, yarns, fabrics, glass, ceramics, and/or metals. In some cases, treating substrates with the complexes can render the substrates less permeable to water and/or oil. The above described chrome complex solutions can be applied as a surface treatment of a variety of materials including, but not limited to, leather by the employment of the methods described in U.S. Pat. No. 3,351,643 and U.S. Pat. No. 3,948,887, herein incorporated by reference.

An embodiment of the present invention also provides for incorporation of the $R_F$ portions into phosphate ester which, in exemplary embodiments, can be used to treat substrates and/or as dispersing agents during the preparation of polymers. Exemplary $R_F$-phosphate esters include $R_F$-$Q_{PE}$, with the $Q_{PE}$ portion being the phosphate portion of the $R_F$-composition. According to exemplary to embodiments the $R_F$ portion can at least partially include an $R_F(R_T)n$ portion as described above. The $R_F(R_T)n$ portion of the ester can also include the $R_S$ portion described above. In accordance with exemplary implementations the $R_S$ portion can be incorporated to provide additional carbon between the $R_F$ and/or $R_F(R_T)n$ portions and the $Q_{PE}$ portion of the ester. Exemplary $R_S$ portions include —$CH_2CH_2$—. Phosphate esters are provided that can include $R_F(R_T)_nQ_{PE}$. The $R_F$ group can include at least two —$CF_3$ groups. The $R_T$ group can include a group having at least two carbons, with n being at least 1. The $Q_{PE}$ group can be a portion of a phosphate ester. $R_F$-phosphate esters, include, but are not limited to, those in Table 9 below.

TABLE 9

Exemplary $R_F$-Phosphate Esters

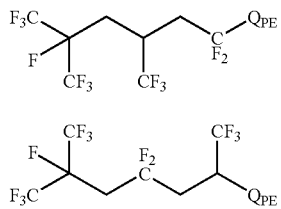

TABLE 9-continued

Exemplary $R_F$-Phosphate Esters

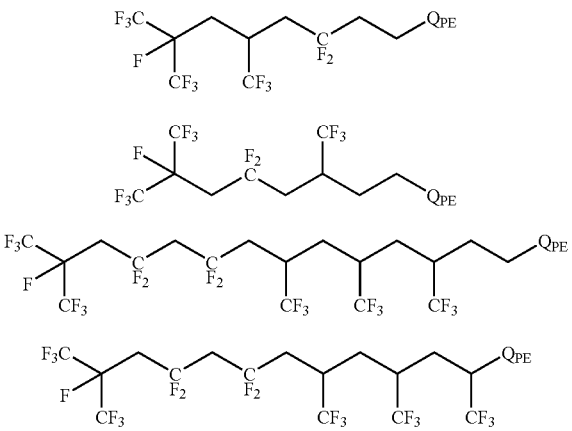

$R_F$-phosphate esters can be used as dispersing agents in the preparation of polymers or they can be diluted and used to treat substrate materials in aqueous baths, for example, by ordinary means such as padding, dipping, impregnating, spraying, etc. These composition can be incorporated into or used to treat such materials as textile fabric, textile yarns, leather, paper, plastic, sheeting, wood, ceramic clays, as well as, manufactured articles of apparel, wallpaper, paper bags, cardboard boxes, porous earthenware, etc. U.S. Pat. No. 3,112,241 describes methods for treating materials using phosphate esters and is herein incorporated by reference. $R_F$-phosphoric acid ester can be used to treat substrates such as wood pulp products, including paper products such as packaging products including food packaging products.

(34)

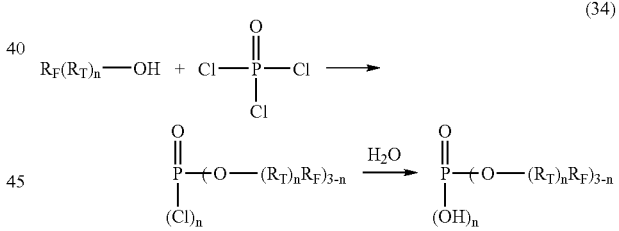

According to scheme (34) above, benzene, pyridine and phosphorous oxychloride (POCl$_3$) can be combined to form mixture A. Mixture A can be chilled to about 7° C., from about 0° C. to about 15° C., and/or about 2° C. To mixture A, a mixture of $R_F(R_T)_n$—OH, pyridine and benzene can be added to form a reaction mixture. The reaction mixture can be allowed to warm to room temperature and heated to reflux and maintained for about one hour to afford a product mixture that can comprise the mono (n=2), bis(n=1) and tris (n=0)$R_F$-phosphate esters. To the product mixture, water can be added to provide a product mixture that can comprise the acid esters of the above acid chlorides.

An embodiment includes the $R_F$ portions incorporated into glycols, such as $R_F$-glycols, including $R_F$-$Q_H$, with $Q_H$ representing the ether portion of the glycol after conjugation or, as hydroxyl functionality before conjugation as the ether. According to exemplary embodiments the $R_F$ portion can at least partially include an $R_F(R_T)_n$ portion as described above. The $R_F(R_T)_n$ portion of the glycol can also include the $R_S$ portion described above. In accordance with exemplary implementations the $R_S$ portion can be incorporated to provide additional carbon between the $R_F$ and/or $R_F(R_T)_n$ portions and the $Q_H$ portion of the glycol. Exemplary $R_S$ portions include —$CH_2$—$CH_2$—. Glycols are provided than can include $R_F(R_T)_nQ_H$. The $R_F$ group can include at least one —$CF_3$ group. The $R_T$ group can include —$CF_2CH_2CH(CF_3)$—, with n being at least 1. The $Q_H$ group can be a portion of a glycol chain backbone. Exemplary $R_F$-glycols include, but are not limited to, those in Table 10 below.

TABLE 10

Exemplary $R_F$-Glycols $R_F$-glycols can be incorporated into polymers such as urethanes including polyurethane elastomers, films and coatings, for example. $R_F$-glycols can be converted to phosphoric acids or phosphate esters of those glycols as well. Referring to scheme 35 below, $R_F$ portions can be incorporated into glycols.

Methods for preparing glycols are described in U.S. Pat. No. 4,898,981, U.S. Pat. No. 5,491,261, U.S. Pat. No. 5,091,550, U.S. Pat. No. 5,132,445, and Dupau, et. al., Adv. Synth. Catal. 2002. 344. No. 3&4, Procedure B, all of which are herein incorporated by reference. For example, and by way of example only, an $R_F$-intermediate (QG=SH) can be reacted with a sulfide diol or 2,6 diox-aspiro (3,3) heptane to produce exemplary $R_F$-glycols ($Q_H$=$H_2CH_2CSH_2CH_2$—). The $R_F$-glycol can be used directly or indirectly to prepare a $R_F$ condensation product such as polyesters, polyureas, polycarbonates and polyurethanes. The glycol functionality can be incorporated into block polymers using $R_F$-glycols. U.S. Pat. No. 5,491,261 discloses several other glycols that can benefit from the RF portion of the present invention and is herein incorporated by reference.

$R_F$-glycols may be converted to phosphoric acid functionality or phosphate esters (not shown). U.S. Pat. Nos. 5,091,550, 5,132,445, 4,898,981 and 5,491,261 all disclose methods of preparing diols and converting diols to phosphate esters and are herein incorporated by reference. In an exemplary implementation, the diols can be converted to phosphoric acids or phosphate esters by reacting diols in the presence of phosphoric acid. These compositions can be incorporated into compounds which can act as oil and/or grease proofing for paper, as well as, soil release agents for textile fibers.

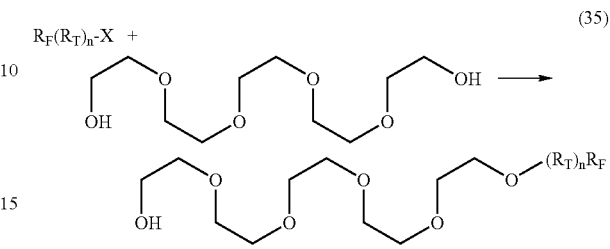

(35)

According to scheme (35) above, pentaethylene glycol and anhydrous tetrahydrofuran (THF) can be combined to form a first mixture. The mixture can be cooled to about 0° C. in an acetone/ice bath. To the first mixture, sodium bis(trimethylsilyl)amide in THF can be added to form a second mixture. The second mixture can be stirred at about 0° C. for about 15 minutes. To the second mixture, the $R_F(R_T)_n$—X, wherein X is a halogen, and THF can be added drop-wise to form a reaction mixture. The reaction mixture can be allowed to warm to room temperature and maintained for about two hours. The reaction mixture can be heated to about 40° C. and maintained for overnight. The reaction mixture can be allowed to cool to room temperature and a 5% (wt/wt) solution of HCl can be added to form a multiphase mixture having a pH of about 7, from which an organic phase can be separated from an aqueous phase. The organic layer can be concentrated in vacuo to afford the $R_F$-glycol. The product structure can be confirmed by NMR and/or chromatographic analysis.

According to another embodiment of the present invention, oligomers, polymers, copolymers, acrylics, and/or resins, for example, can be prepared that include an $R_F$-monomer unit, such as $R_F$-$Q_{MU}$. The monomer unit portion, $Q_{MU}$, can be a single unit within a complex of units and the monomer unit need not repeat within the complex. In an exemplary embodiment, the monomer unit can be a single unit within the complex or it may be one of many identical units linked together, such as a homopolymer, for example. The complex can also include block polymers and/or polyurethane resins. The $R_F$ of the unit can include a pendant group of the monomer unit. The monomer unit may be associated with a complex, perhaps even bonded to the complex, for example, and $Q_{MU}$ can include the portion of the monomer unit that is associated with the complex. The complex may be coated onto a substrate or it may be chemically bonded to the substrate. For example, a preparation of $R_F$-intermediates can be provided to the substrate and groups such as hydroxyl groups common to substrates like cotton, may provide sites that allow the $R_F$-intermediate to chemically bond to the substrate when forming part of, or being associated with a complex. In an exemplary embodiment, $Q_{MU}$ can represent the acrylate functionality of an acrylic and $R_F$ can be a pendant group from the acrylics chain and/or backbone. Polymers comprising $R_F(R_T)_nQ_{MU}$ are provided. The $R_F$ group can include at least one —$CF_3$ group. The $R_T$ group can include —$CF_2CH_2CH(CF_3)$—, with n being at least 1. The $Q_{MU}$ group can be a portion of a polymer chain backbone. Exemplary. $R_F$-monomer units include but are not limited to those in Table 11 below.

TABLE 11

Exemplary $R_F$-Monomer Units (structures shown)

In exemplary embodiments oligomers containing a $R_F$-monomer unit can be prepared from $R_F$-monomers. $R_F$-monomers can include $R_F$-intermediates above, but may contain functionality that allows for their conjugation with another monomer, but not necessarily the same $R_F$-monomer. The monomers can include $R_F(R_T)_n Q_M$. The $R_F$ group can include at least one —$CF_3$ group. The $R_T$ group can include —$CF_2CH_2CH(CF_3)$—, with n being at least 1. The $Q_M$ group can be at least one atom of the periodic table of elements. Exemplary $R_F$-monomers include, but are not limited to those in Table 12 below.

TABLE 12

Exemplary $R_F$-Monomer Units (structures shown)

Referring to scheme (36) below, multiple reactions sequences are shown for the preparation of $R_F$-monomers having the $R_F$ group.

(36)

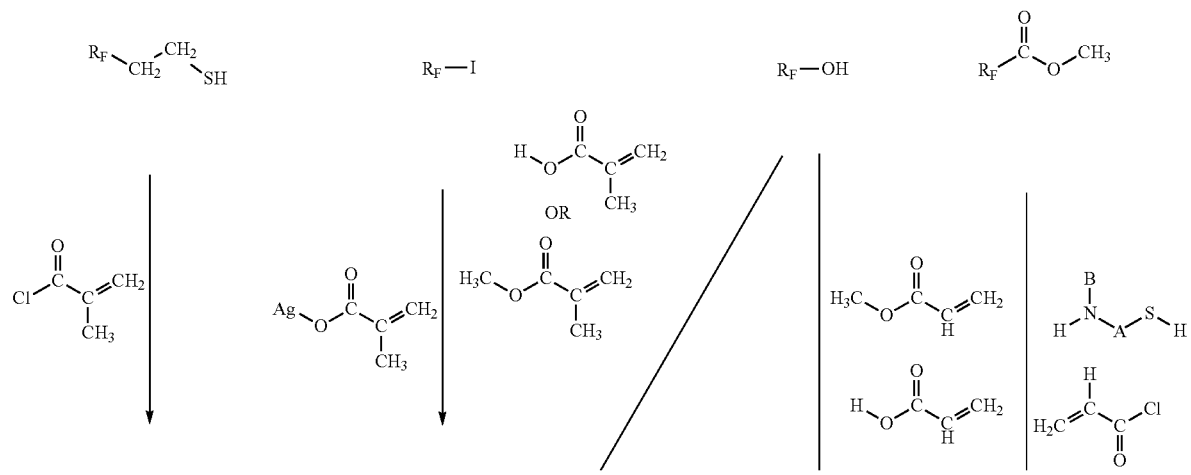

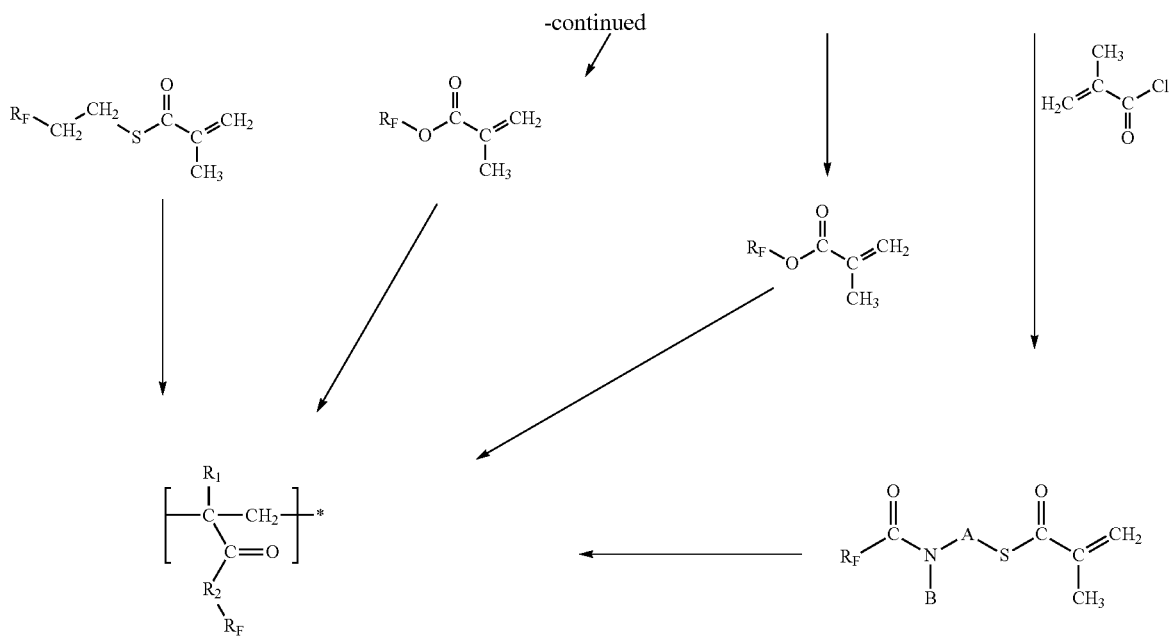

U.S. Pat. Nos. 3,491,169, 3,282,905, 3,497,575, 3,544,663, 6,566,470, 4,147,851, 4,366,299, 4,439,329, and 5,439,998 all relate to the use and preparation of acrylic emulsion polymers that can benefit from the $R_F$ groups and, are herein incorporated by reference. Thiol $R_F$-intermediates, iodine $R_F$-intermediates, hydroxyl $R_F$-intermediates, and/or acetate $R_F$-intermediates can be converted to $R_F$-monomers according to scheme (35) above, and these $R_F$-monomers can be used to prepare a composition containing an $R_F$-monomer unit.

For example, and by way of example only, the $R_F$ portion can be incorporated into a $R_F$-monomer as described in U.S. Pat. No. 6,566,470 represented as $R_F$—W—X—C(=O)—C($R_1$)=$CH_2$, with the $R_F$ portion as described above. W can be an alkylene with 1 to 15 carbons, hydroxyalkylene with 3 to 15 carbons, —($C_nH_{2n}$)($OC_mH_{2m}$)$_q$—, —$SO_2NR_2$—($C_nH_{2n}$)—, or —$CONR_2$—($C_nH_{2n}$)—, with n being 1 to 12, m being 2 to 4, q being 1 to 10, and $R_1$ being an alkyl group with 1 to 4 carbon atoms, for example, X being O, S and/or $N(R_2)$, where $R_2$ is as $R_1$.

(37)

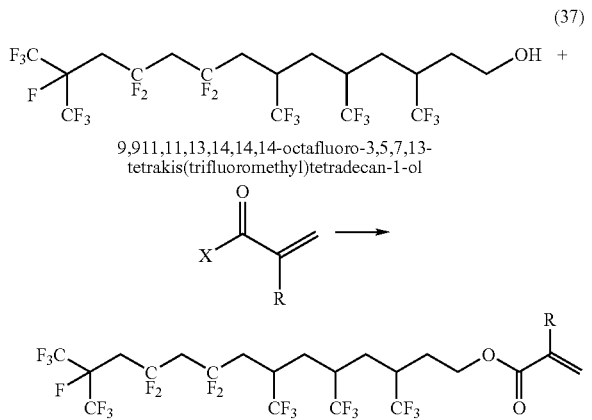

9,9,11,11,13,14,14,14-octafluoro-3,5,7,13-tetrakis(trifluoromethyl)tetradecan-1-ol According to scheme (37) and procedures set forth in the published international applications, $R_F$-acrylates can be prepared wherein R=$CH_3$ or H and X is a halogen. The resulting acrylates can be homopolymerized and/or copolymerized according to the general procedures listed in the published international applications. For example and by way of example only, solutions of $R_F$-monomers can be provided to a substrate and allowed to complex, for example, via evaporating the solvent of the solution to form a complex that includes a $R_F$-monomer unit, providing these solutions to a substrate such as glass, nylon, and/or cotton and allowing the $R_F$-monomer to become part of a complex, such as coating the substrate.

The surface energy of the complex can be determined using the standard Fowkes method using diiodomethane and water as probe liquids, and the Zisman method of surface energy analysis using octane, decane, tetradecane, and hexadecane as probe liquids. Contact angle of drops of Zisman probe liquids, as well as the Fowkes probes, can be determined using a Kruss prop Shape Analysis System.

$R_F$-monomers can be incorporated with other monomers and then incorporated into the construction of paper materials or used to treat paper materials. $R_F$-monomers can also be used to prepare polymer solutions. Polymeric solutions can be diluted to a percentage aqueous or non-aqueous solution and then applied to substrates to be treated, such as paper plates.

$R_F$-monomers can also be incorporated into copolymers with comonomers such as the dialkyl amino alkyl acrylate or methacrylate or acrylamide or methacrylamide monomer and its amine salt quaternary ammonium or amine oxide form, as described in U.S. Pat. No. 4,147,851, herein incorporated by reference. The general formula for $R_F$-monomers can be $R_F$q$O_2$CC(R)=$CH_2$, with R being H or $CH_3$, q being an alkylene of 1 to 15 carbon atoms, hydroxyalkylene of 3 to 15 carbon atoms, or $C_nH_{2n}$($OC_qH_{2q}$)$_m$—, —$SO_2NR_1$($C_nH_{2n}$)—, or —$CONR_1$($C_nH_{2n}$)—, n being 1 to 15, q being 2 to 4, and m being 1 to 15. Monomers used to form copolymers with acrylates and the $R_F$-monomers include those having amine functionality. These copolymers can be diluted in a solution and applied or incorporated directly into or on substrates to be treated, such as paper.

$R_F$-monomers can also be used to form acrylate polymers or other acrylate monomers consistent with those described in U.S. Pat. No. 4,366,299, herein incorporated by reference. As described, $R_F$-monomers can be incorporated into paper products or applied thereon.

$R_F$-monomers, acrylates and/or acrylics, for example, can be applied to finished carpet or incorporated into the finished carpet fiber before it is woven into carpet. $R_F$-monomers can be applied to carpet by a normal textile finishing process known as padding, in which the carpet is passed through a bath containing the $R_F$-monomer and, for example, latex, water, and/or other additives such as non-rewetting surfaces. The carpet can then be passed through nip rollers to control the rate of the add-on before being dried in a tenter frame.

$R_F$-monomers may also be incorporated into the fiber by reacting the fiber with $R_F$-intermediates having isocyanate functionality, $R_F$-isocyanate, for example.

$R_F$ portions can also be incorporated into materials used to treat calcitic and/or siliceous particulate materials. For example, $R_F$-monomers can be incorporated into a copolymer where the copolymer can either be part of a formulation to treat these materials or used by itself to treat these materials as described in U.S. Pat. No. 6,383,569, herein incorporated by reference. The $R_F$-monomer can have the general formula $R_F$-Q-A-C(O)—C(R)=CH$_2$ wherein $R_F$ is described above, R is H or CH$_3$, A is O, S, or N(R$_1$), wherein R$_1$ is H or an alkyl of from 1 to 4 carbon atoms, Q is alkylene of 1 to about 15 carbon atoms, hydroxyalkylene of 3 to about 15 carbon atoms, —(C$_n$H$_{2n}$)(OC$_q$H$_{2q}$)$_m$—, —SO$_2$—NR$_1$(C$_n$H$_{2n}$)—, or —CONR$_1$(C$_n$H$_{2n}$)—, wherein R$_1$ is H or an alkyl of 1 to 4 carbon atoms, n is 1 to 15, q is 2 to 4, and m is 1 to 15.

$R_F$-compositions and mixtures containing the $R_F$ portion can be used to treat substrates including hard surfaces like construction materials such as brick, stone, wood, concrete, ceramics, tile, glass, stucco, gypsum, drywall, particle board, and chipboard. These compositions and mixtures can be used alone or in combination with penetration assistance such as non-ionic surfactants. These compositions can be applied to the surface of calcitic and/or siliceous architectural construction material by known methods, for example, by soaking, impregnation, emersion, brushing, rolling, or spraying. The compositions can be applied to the surface to be protected by spraying. Suitable spraying equipment is commercially available. Spraying with a compressed air sprayer is an exemplary method of application to the particular substrate. U.S. Pat. Nos. 6,197,382 and 5,674,961 also describe methods for applying and using polymer solutions and are herein incorporated by reference.

In an exemplary process of producing solutions having components with $R_F$, an $R_F$-intermediate having a methyl-epoxide functionality may be condensed with a monocarboxylic alkenoic acid to prepare an unsaturated $R_F$-ester (not shown). Exemplary methods for producing these kinds of unsaturated esters are described in U.S. Pat. No. 5,798,415, herein incorporated by reference. Additional esters may be prepared according to U.S. Pat. No. 4,478,975, herein incorporated by reference. Components of these solutions can also include dimethyl amino ethyl methacrylate, and these components can be applied in organic and inorganic solvents, as described in U.S. Pat. No. 6,120,892 herein incorporated by reference. $R_F$-monomers can also be combined with other monomers to produce copolymers or in solutions with amido and sulfur monomers as described by U.S. Pat. No. 5,629,372 herein incorporated by reference.

$R_F$-intermediates having amine functionality can also be reacted with tetrachlorophthalic anhydride using U.S. Pat. No. 4,043,923 as an exemplary reaction scheme (not shown). U.S. Pat. No. 4,043,923 is herein incorporated by reference. The reaction product can be mixed with a carpet cleaning solution to provide soil repellency.

In exemplary embodiments urethanes containing a $R_FQ_U$ ($R_F$-Urethanes) can be prepared from $R_F$-Intermediates. $R_F$-Urethanes can include $R_F$-intermediates above, but may contain functionality that allows for their conjugation with another $R_FQ_U$ compounds, but not necessarily the same $R_FQ_U$ compound. According to exemplary embodiments the $R_F$ portion of the urethane can at least partially include an $R_F(R_T)_n$ portion as described above. The $R_F(R_T)_n$ portion of the urethane can also include the $R_S$ portion described above. In accordance with exemplary implementations the $R_S$ portion can be incorporated to provide additional carbon between the $R_F$ and/or $R_F(R_T)_n$ portions and the $Q_U$ portion of the urethane. Exemplary $R_s$ portions include —CH$_2$—CH$_2$—. Urethanes comprising $R_F(R_T)_nQ_U$ are provided. The $R_F$ group can include at least one —CF$_3$ group. The $R_T$ group can include —CF$_2$CH$_2$CH(CF$_3$)—, with n being at least 1. The $Q_U$ group can be at least one atom of the periodic table of elements. Exemplary $R_F$-urethanes, such as $R_F$-$Q_U$, can include, but are not limited to those listed in Table 13 below.

TABLE 13

Exemplary $R_F$-Urethanes

F$_3$C—CF(F)—CH$_2$—CH(CF$_3$)—CH$_2$—CF$_2$—Q$_U$

F—C(CF$_3$)(F$_3$C)—CF$_2$—CH(CF$_3$)—CH(CF$_3$)—Q$_U$

F$_3$C—CF(F)—CH$_2$—CH(CF$_3$)—CH$_2$—CF$_2$—CH$_2$—Q$_U$

F—C(CF$_3$)(F$_3$C)—CF$_2$—CH(CF$_3$)—CH(CF$_3$)—CH$_2$—Q$_U$

F$_3$C—CF(F)—CF$_2$—CF$_2$—CH(CF$_3$)—CH(CF$_3$)—CH(CF$_3$)—CH$_2$—Q$_U$

F$_3$C—CF(F)—CF$_2$—CF$_2$—CH(CF$_3$)—CH(CF$_3$)—CH(CF$_3$)—CH$_2$—Q$_U$

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A surfactant composition comprising $R_F(R_T)_nQ_s$, wherein:

the $R_F$ group is —CF$_3$; C$_3$F$_6$—; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;

the $R_T$ group comprises —CF$_2$CH$_2$CH(CF$_3$)—;

n is at least 1; and the $Q_S$ group is halogen, mercaptan, thiocyanate, sulfonyl chloride, hydroxyl, cyano, acetate, allyl, epoxide, acrylic ester, ether, sulfate, phosphate, amine, —(CH$_2$)$_n$—S(O)$_2$NH—(CH$_2$)$_3$NH$_2^+$Cl$^-$, —(CH$_2$)$_n$S(O)$_2$NH(CH$_2$)$_3$NH$_2^+$O$^-$, —(CH$_2$)$_n$S(O)$_2$NH—(CH$_2$)$_3$—NH$_2^+$CH$_2$C(O)O$^-$, or —(CH$_2$)$_n$S(O)$_2$N(CH$_2$CH$_3$)NH$_2$(CH$_2$)C(O)O$^-$K$^+$ wherein n is 0 to 4.

2. The surfactant of claim 1 wherein the $R_F$ group is one of —C$_3$F$_6$ or —C$_3$F$_7$.

3. The surfactant of claim 1 wherein the $R_T$ group comprises —CH$_2$CF$_2$CH$_2$CH(CF$_3$)—.

4. A foam stabilizer composition comprising $R_F(R_T)_n Q_{FS}$, wherein:
the $R_F$ group is —CF$_3$; C$_3$F$_6$—; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_{FS}$ group is halogen, mercaptan, thiocyanate, sulfonyl chloride, hydroxyl, cyano, acetate, allyl, epoxide, acrylic ester, ether, sulfate, phosphate, amine, or polyalkoxylated amines.

5. The foam stabilizer of claim 4 wherein the $R_T$ group comprises —CH$_2$CF$_2$CH$_2$CH(CF$_3$)—.

6. The foam stabilizer of claim 4 wherein the $R_T$ group comprises —CF$_2$CH$_2$CF$_2$CH$_2$CH(CF$_3$)—.

7. A monomer comprising $R_F(R_T)_n Q_M$, wherein:
the $R_F$ group is —CF$_3$; C$_3$F$_6$—; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$)$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_M$ group is at least one atom of the periodic table of elements.

8. The monomer of claim 7 wherein the $R_T$ group comprises —CH$_2$CF$_2$CH$_2$CH(CF$_3$)—.

9. The monomer of claim 7 wherein the $R_T$ group comprises $^-$CF$_2$CH$_2$CF$_2$CH$_2$CH(CF$_3$)—.

10. A polymer comprising $R_F(R_T)_n Q_{MU}$, wherein:
the $R_F$ group is —CF$_3$; C$_3$F$_6$—; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_{MU}$ group is an acrylate functionality.

11. The polymer of claim 10 wherein the $R_F$ group is one of —C$_3$F$_6$ or —C$_3$F$_7$.

12. The polymer of claim 10 wherein the $R_T$ group comprises —CH$_2$CF$_2$CH$_2$CH(CF$_3$)—.

13. A urethane comprising $R_F(R_T)_n Q_U$, wherein:
the $R_F$ group is —CF$_3$; C$_3$F$_6$—; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_U$ group is at least one atom of the periodic table of elements.

14. The urethane of claim 13 wherein the RF group is one of —C$_3$F, or —C$_3$F$_7$.

15. The urethane of claim 13 wherein the $R_T$ group comprises —CH$_2$CF$_2$CH$_2$CH(CF$_3$)—.

16. A glycol comprising $R_F(R_T)_n Q_H$, wherein:
the $R_F$ group is —CF$_3$; C$_3$F$_6$—; C$_3$F$_7$; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_H$ group is a portion of a glycol chain backbone.

17. The glycol of claim 16 wherein the $R_F$ group is one of —C$_3$F$_6$ or —C$_3$F$_7$.

18. The glycol of claim 16 wherein the $R_T$ group comprises —CH$_2$CF$_2$CH$_2$CH(CF$_3$)—.

19. A metal complex comprising $R_F(R_T)_n Q_{MC}$, wherein:
the $R_F$ group is —CF$_3$; C$_3$F$_6$; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_{MC}$ group comprises a charged group configured to complex one or more metal ions.

20. The metal complex of claim 19 wherein the $R_F$ group is one of —C$_3$F$_6$ or C$_3$F$_7$.

21. The metal complex of claim 19 wherein the $R_T$ group comprises —CH$_2$CF$_2$CH$_2$CH(CF$_3$)—.

22. A phosphate ester composition comprising $R_F(R_T)_n Q_{PE}$, wherein:
the $R_F$ group is —CF$_3$; C$_3$F$_6$; C$_3$F$_7$—; (CF$_3$)$_2$CF—; (CF$_3$)$_2$CF(CH$_2$)—; (CF$_3$)$_3$C—; (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CH$_2$CH(CF$_3$)—;
n is at least 1; and
the $Q_{PE}$ group is a portion of a phosphate ester.

23. The phosphate ester of claim 22 wherein the $R_F$ group is one of —C$_3$F$_6$ or —C$_3$F$_7$.

24. The phosphate ester of claim 22 wherein the $R_T$ group comprises CH$_2$CF$_2$CH$_2$CH(CF$_3$)—.

25. A composition comprising $R_F(R_T)_n Q_g$, wherein:
the $R_F$ group is (CF$_3$)$_3$CCF$_2$—; (CF$_3$)$_3$CCF$_2$(CH$_2$)$_p$—; (CF$_3$)$_2$CF(CH$_2$CF$_2$)$_l$—; (CF$_3$)$_2$CF(CH$_2$C(CF$_3$)H)$_m$—; (CF$_3$)$_2$CF(CH$_2$CF$_2$)$_l$(CH$_2$C(CF$_3$)H)$_m$; or (CF$_3$)$_3$C(CH$_2$C(CF$_3$)H)$_m$; wherein l is 1 to 2; m is 1 to 3; and p is 5;
the $R_T$ group comprises —CF$_2$CX$_2$— wherein each X is independently H or F;
n is greater than 1; and
the Qg group is at least one atom of the periodic table of elements.

26. The composition of claim 25 wherein the $R_F$ group has a carbon amount between C5 and C17.

27. The composition of claim 25 wherein the $R_T$ group comprises —CH$_2$CH$_2$—.

28. The composition of claim 25 wherein the $R_T$ group comprises —CH$_2$CF$_2$—.

29. The composition of claim 25 wherein the $R_F$ group is (CF$_3$)$_2$CF(CH2CF$_2$)$_l$—, l being from 1 to 2.

* * * * *